US010138178B1

(12) United States Patent
Hossain et al.

(10) Patent No.: US 10,138,178 B1
(45) Date of Patent: *Nov. 27, 2018

(54) OXIDATIVE CRACKING OF ALKANES WITH FLUIDIZED VANADIUM CATALYST

(71) Applicant: KING FAHD UNIVERSITY OF PETROLEUM AND MINERALS, Dhahran (SA)

(72) Inventors: Mohammad Mozahar Hossain, Dhahran (SA); AbdAlwadood Hassan Elbadawi, Dhahran (SA); Muhammad Yasir Khan, Dhahran (SA); Shaikh Abdur Razzak, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,863

(22) Filed: Jul. 13, 2018

Related U.S. Application Data

(63) Continuation of application No. 15/237,210, filed on Aug. 15, 2016, now Pat. No. 10,053,400.

(51) Int. Cl.
*B01J 21/04* (2006.01)
*B01J 23/10* (2006.01)
(Continued)

(52) U.S. Cl.
CPC .............. *C07C 4/06* (2013.01); *B01J 23/22* (2013.01); *B01J 35/0026* (2013.01);
(Continued)

(58) Field of Classification Search
CPC ....... C07C 4/026; C07C 4/06; C07C 2523/10; C07C 2523/22; B01J 21/04; B01J 23/10;
(Continued)

(56) References Cited

U.S. PATENT DOCUMENTS 3,207,808 A  9/1965  Bajars
4,957,892 A  9/1990  Yoo
(Continued)

FOREIGN PATENT DOCUMENTS

DE    102012206543 A1   10/2013
EP       0556489 A1    8/1993

OTHER PUBLICATIONS

Balzer, R., et al., "Catalytic Oxidation of Volatile Organic Compounds (N-Hexane, Benzene, Toluene, O-Xylene) Promoted by Cobalt Catalysts Supported on $\gamma$-$Al_2O_3$—$CeO_2$", Brazilian Journal of Chemical Engineering, vol. 31, No. 3, 14 Pages total, (2014).

(Continued)

*Primary Examiner* — Patricia L. Hailey
(74) *Attorney, Agent, or Firm* — Oblon, McClelland, Maier & Neustadt, L.L.P.

(57) ABSTRACT

Fluidizable catalysts for the gas phase oxygen-free oxidative cracking of alkanes, such as hexane, to one or more olefins, such as ethylene, propylene, and/or butylene. The catalysts comprise 1-15% by weight per total catalyst weight of one or more vanadium oxides ($VO_x$), such as $V_2O_5$. The catalysts are disposed on an alumina support that is modified with cerium to influence catalyst acidity and characteristics of lattice oxygen at the catalyst surface. Various methods of preparing and characterizing the catalyst as well as methods for the gas phase oxygen free oxidative cracking of alkanes, such as hexane, to one or more olefins, such as ethylene, propylene, and/or butylene with improved alkane conversion and olefins product selectivity are also disclosed.

14 Claims, 5 Drawing Sheets

(51) Int. Cl.
*C07C 4/06* (2006.01)
*C07C 4/02* (2006.01)
*B01J 37/14* (2006.01)
*B01J 37/18* (2006.01)
*B01J 37/04* (2006.01)
*B01J 35/10* (2006.01)
*B01J 35/00* (2006.01)
*B01J 35/02* (2006.01)
*B01J 23/22* (2006.01)

(52) U.S. Cl.
CPC ......... *B01J 35/023* (2013.01); *B01J 35/1014* (2013.01); *B01J 35/1019* (2013.01); *B01J 37/04* (2013.01); *B01J 37/14* (2013.01); *B01J 37/18* (2013.01); *C07C 4/025* (2013.01); *C07C 2521/04* (2013.01); *C07C 2523/10* (2013.01); *C07C 2523/22* (2013.01)

(58) Field of Classification Search
CPC ...... B01J 23/22; B01J 35/0006; B01J 35/023; B01J 35/026; B01J 35/1009; B01J 35/1014; B01J 35/1019; B01J 37/04; B01J 37/14; B01J 37/18
USPC ................. 585/654, 651; 208/106, 113, 122; 502/304, 353–355
See application file for complete search history.

(56) References Cited

U.S. PATENT DOCUMENTS

| | | | |
|---|---|---|---|
| 5,220,092 A | 6/1993 | Clark et al. | |
| 5,284,643 A | 2/1994 | Morrison | |
| 10,053,400 B2 * | 8/2018 | Hossain | C07C 4/06 |
| 2003/0065235 A1 | 4/2003 | Allison | |
| 2003/0166984 A1 | 9/2003 | Park | |
| 2011/0245571 A1 | 10/2011 | Kustov et al. | |

OTHER PUBLICATIONS

Al-Ghamdi, S., et al., "$VO_x$/c-$Al_2O_3$ Catalyst for Oxidative Dehydrogenation of Ethane to Ethylene: Desorption Kinetics and Catalytic Activity", Applied Catalysis A: General, vol. 450, pp. 120-130, (2013).

Boyadjian, C., et al., "Catalytic Oxidative Cracking of Hexane as a Route to Olefins", Applied Catalysis A: General, vol. 372, pp. 167-174, (2010).

Elbadawi, A.H., et al., "Kinetics of Oxidative Cracking of Hexane to Olefins over $VO_x$/Ce—$Al_2O_3$ in a Gas Phase Oxygen Free Environment", International Symposia on Chemical Reaction Engineering, 2 Pages total, (Jun. 13, 2016).

* cited by examiner

OXIDATIVE CRACKING OF ALKANES WITH FLUIDIZED VANADIUM CATALYST

CROSS-REFERENCE TO RELATED APPLICATIONS

The present application is a Continuation of U.S. patent application Ser. No. 15/182,248 (now U.S. Pat. No. 10,053,400), having a filing date of Aug. 15, 2016.

BACKGROUND OF THE INVENTION

Technical Field

The present disclosure relates to fluidizable vanadium based $VO_x/Ce$-γ-$Al_2O_3$ catalysts and processes using the catalysts for the cracking of alkanes to olefins, such as hexane to propylene, in the absence of gas phase oxygen.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Olefins such as ethylene and propylene are important feedstock in the chemical industry. They are used for the production of polyethylene, polypropylene and other industrial intermediates. Conventionally, olefins are obtained by steam cracking and catalytic conversion of ethanol. Steam cracking processes suffer from high production costs due to the use of petroleum feedstock and the energy consumption in the furnace [T. Ren, M. Patel, and K. Blok, "Olefins from conventional and heavy feedstocks: Energy use in steam cracking and alternative processes," *Energy*, vol. 31, pp. 425-451, 2006.]. Additionally, ethane crackers as well as the retrofitting of naphtha crackers were developed after the rise of shale oil technology over the past decades [N. Rahimi and R. Karimzadeh, "Catalytic cracking of hydrocarbons over modified ZSM-5 zeolites to produce light olefins: A review," *Appl. Catal. A Gen.*, vol. 398, no. 1-2, pp. 1-17, 2011; and B. Yilmaz and U. Müller, "Catalytic applications of zeolites in chemical industry," *Top. Catal.*, vol. 52, pp. 888-895, 2009.—each incorporated herein by reference in its entirety]. Furthermore, olefins are produced from methanol using zeolite processes such as the methanol to olefins (MTO) process. The two commonly used catalysts in this process are ZSM-5 (MFI-type) and SAPO-34 (CHA-type). MFI is a medium pore sized alumina-silicate with ten membered ring pores. MFI is highly selective toward propylene and butylene; however, the yield of short olefins is less than in SAPO-34. SAPO-34 is a silico-alumino-phosphate with small eight-membered ring pores, which has high selectivity towards ethylene but suffers from fast deactivation due to coke formation [D. Chen, K. Moljord, and a. Holmen, "A methanol to olefins review: Diffusion, coke formation and deactivation on SAPO type catalysts," *Microporous Mesoporous Mater.*, vol. 164, pp. 239-250, 2012; and S. Askari, R. Halladj, and M. Sohrabi, "Methanol conversion to light olefins over sonochemically prepared SAPO-34 nanocatalyst," *Microporous Mesoporous Mater.*, vol. 163, pp. 334-342, 2012; and G. Liu, P. Tian, Q. Xia, and Z. Liu, "An effective route to improve the catalytic performance of SAPO-34 in the methanol-to-olefin reaction," *J. Nat. Gas Chem.*, vol. 21, no. 4, pp. 431-434, 2012.—each incorporated herein by reference in its entirety]. Therefore, in general zeolites have deactivation problems and generally low selectivity to olefins (i.e. less than 50%) [Mamedov, E. A. Corberfin, V. Cortds "Oxidative dehydrogenation of lower alkanes on vanadium oxide-based catalysts. The present state of the art and outlooks" *Appl. Catal. A Gen.*, vol. 127, pp. 1-40, 1995; and J. Li, Y. Wei, G. Liu, Y. Qi, P. Tian, B. Li, Y. He, and Z. Liu, "Comparative study of MTO conversion over SAPO-34, H-ZSM-5 and H-ZSM-22: Correlating catalytic performance and reaction mechanism to zeolite topology," *Catal. Today*, vol. 171, no. 1, pp. 221-228, 2011; and J. Lefevere, S. Mullens, V. Meynen, and J. Van Noyen, "Structured catalysts for methanol-to-olefins conversion: a review," *Chem. Pap.*, vol. 68, no. 9, pp. 1143-1153, 2014.]. Catalytic cracking of hexane is another promising process to produce short olefins, in these processes many types of catalyst have been used including metal oxides as well as zeolites. Zeolites have been tested for n-hexane cracking to propylene, such as the zeolite MCM-22 with various Si/Al ratios [Y. Wang, T. Yokoi, S. Namba, J. N. Kondo, and T. Tatsumi, "Catalytic cracking of n-hexane for producing propylene on MCM-22 zeolites," *Appl. Catal. A Gen.*, 2014.—incorporated herein by reference in its entirety]. Propylene selectivity was found to be 40% at a Si/Al ratio of 62. ZSM-5 zeolites were also investigated using methanol coupling [F. Chang, Y. Wei, X. Liu, Y. Qi, D. Zhang, Y. He, and Z. Liu, "An improved catalytic cracking of n-hexane via methanol coupling reaction over HZSM-5 zeolite catalysts," *Catal. Letters*, vol. 106, no. February, pp. 171-176, 2006.—incorporated herein by reference in its entirety]. Methanol contributed positively to the reaction by decreasing the activation energy which ultimately led to an increased olefins yield. Another study investigated the cracking of hydrocarbons over a ZSM-5 catalyst with different Si/Al ratios [B. Lücke, A. Martin, H. Günschel, and S. Nowak, "CMHC: coupled methanol hydrocarbon cracking," *Microporous Mesoporous Mater.*, vol. 29, pp. 145-157, 1999.—incorporated herein by reference in its entirety]. The catalyst was also modified using iron (Fe) to decrease catalyst deactivation; this increased the yield of olefins to as high as 305. In addition, metal oxides, such as $MoO_2$ were considered as potential catalysts for n-hexane cracking obtaining a total olefins yield of 85% [J. H. Song, P. Chen, S. H. Kim, G. a. Somorjai, R. J. Gartside, and F. M. Dautzenberg, "Catalytic cracking of n-hexane over MoO2," *J. Mol. Catal. A Chem.*, vol. 184, pp. 197-202, 2002.—incorporated herein by reference in its entirety]. Catalytic oxidative cracking is a potential alternative to steam cracking due to factors including: (i) an exothermic oxidation reaction, (ii) an adiabatic process, and (iii) a reduced coke formation. Although, for the non-catalytic pyrolysis of hexane at 750° C. the oxygen feed was found to increase reaction rate and give a conversion of 85% with an olefin selectivity of 59% and ethylene as the major product [Xiaoyin Chena, Yong Liua, Guoxing Niub, Zhuxian Yanga, Maiying Biana, Adi Hea, "High temperature thermal stabilization of alumina modified by lanthanum species" *React. Kinet. Catal. Lett*, vol. 81, no. 2, pp. 203-209, 2001.—incorporated herein by reference in its entirety]. The presence of oxygen allows the cracking to proceed in an autothermal way, where the exothermic reaction provides the heat for the cracking reaction. Liu, et al. conducted a comprehensive study of homogeneous gas phase versus heterogeneous catalytic oxidative cracking of hexane at a temperature of 700° C. [H. X. X. Liu, W. Li, H. Zhu, Q. Ge, Y. Chen, "Light Alkenes Preparation by the Gas Phase Oxidative Cracking or Catalytic Oxidative Cracking of High Hydrocarbons", *Catal. Lett.*, vol. 94, no. 1-2, pp. 31-36, 2004.—incorporated herein by reference in its entirety]. Amongst the catalysts tested, 0.25 wt % Li/MgO showed the best performance (64 mol % conversion of hexane and 67 mol % selectivity to olefins). However, due to the high reaction temperature, the gas phase reaction had the major role and the presence of catalyst had no major influence on conversions of hexane and yields of olefins. Li/MgO catalysts with different promoters (i.e. MoO3, Bi2O3, V2O5) were tested for oxidative cracking of n-hexane and the olefin selectivity obtained was up to 50% [C. Boyadjian, B. Van Der Veer, I. V. Babich, L. Lefferts, and K. Seshan, "Catalytic oxidative cracking as a route to olefins: Oxidative conversion of hexane over MoO3-Li/MgO," *Catal. Today*, vol. 157, pp. 345-350, 2010.—incorporated herein by reference in its entirety].

Oxidative cracking of n-hexane over supported metal oxides is a potential synthetic route for the production of short olefins. Studies have shown that the presence of metal oxide catalysts during cracking enhances yield of olefins. This observation can be explained qualitatively with a mechanism that includes activation of the alkane on the catalyst generating alkyl radicals that undergo a radical-chain mechanism in the gas phase. In this mechanism oxygen has two functions. First, the presence of small amounts of oxygen influences the radical gas phase chemistry significantly because the type and concentration of the chain propagator radicals are greatly increased. At higher oxygen partial pressures the radical chemistry is only slightly influenced by the increasing oxygen concentration. The second function of oxygen is to facilitate the removal of hydrogen from the surface OH-species that are formed during the activation of alkane on the catalyst. Therefore, it has been shown that the oxidative conversion of propane over Li/MgO catalysts follows a mixed heterogeneous-homogeneous radical chemistry where the catalyst acts as an initiator [L. Leveles, K. Seshan, J. A. Lercher, and L. Lefferts, "Oxidative conversion of propane over lithium-promoted magnesia catalyst—I. Kinetics and mechanism," *J. Catal.*, vol. 218, pp. 296-306, 2003.—incorporated herein by reference in its entirety]. Hence, the mentioned mechanism was used to study n-hexane cracking over Li/MgO modified catalysts, and it was proposed that hexane is activated before the cracking reaction takes place. The study also showed that the catalyst increases the production of olefins via dehydrogenation. Oxidative cracking of n-hexane to olefins is a promising process; however, all previous work was done using fixed-bed reactors and gas phase oxygen as a co-reactant for the purpose of dehydrogenation. This setup induces $CO_x$ formation by combustion due to the presence of oxygen and therefore a lower yield of olefins is obtained.

In view of the forgoing, one aspect of the present invention is to provide fluidizable oxidative cracking catalysts comprising vanadium oxide catalytic species using a mixed Ce-γ-$Al_2O_3$ as support material. The physiochemical characterization of the catalysts offers an examination of the $VO_x$ monovanadate and polyvanadate surface species on the support, the catalyst's stability, level of acidity and metal-support interactions. A further aim of the present disclosure is to provide methods for producing these $VO_x$/Ce—$Al_2O_3$ catalysts. An additional aim of the present disclosure is to provide methods for the oxidative cracking of alkanes, such as hexane, to produce one or more olefins, such as ethylene, propylene, and/or butylene employing the lattice oxygen of these $VO_x$/Ce—$Al_2O_3$ catalysts. These catalysts present relatively high acidity enhancing the cracking reaction, and simultaneously the catalyst lattice oxygen allows dehydrogenation of alkanes to olefins to take place (FIG. 1). These methods may be performed in a gas phase oxygen free environment under fluidized bed reaction conditions that enhance catalyst-feed contact at different temperatures and reaction times accomplishing high alkane conversion and high olefins product selectivity over $CO_x$ combustion products.

BRIEF SUMMARY OF THE INVENTION

According to a first aspect, the present disclosure relates to a catalyst comprising i) a support material comprising alumina modified by cerium and ii) a catalytic material comprising one or more vanadium oxides disposed on the support material, wherein the catalyst comprises 1-15% of the one or more vanadium oxides by weight relative to the total weight of the catalyst.

In one embodiment, the catalyst comprises 0.05-1.0% of cerium by weight relative to the total weight of the catalyst.

In one embodiment, the one or more vanadium oxides form an amorphous phase on the surface of the support material.

In one embodiment, the one or more vanadium oxides form a crystalline phase on the surface of the support material.

In one embodiment, the one or more vanadium oxides are at least one selected from the group consisting of $V_2O_5$, $VO_2$, and $V_2O_3$.

In one embodiment, the catalyst comprises at least 50% of $V_2O_5$ by weight relative to the total weight of the one or more vanadium oxides.

In one embodiment, the catalyst has an average particle size in the range of 20-160 μm.

In one embodiment, the catalyst has an apparent particle density in the range of 1-10 g/cm³.

In one embodiment, the catalyst has a BET surface area in the range of 2-50 m²/g.

In one embodiment, the catalyst is fluidizable and has Class B powder properties in accordance with Geldart particle classification.

According to a second aspect, the present disclosure relates to a method for producing the catalyst of the present disclosure in any of its embodiments comprising i) mixing an aluminum salt or hydrate with a cerium salt or hydrate in a solvent to form an alumina precursor solution, ii) adding a base to and hydrolyzing the alumina precursor solution to form the support material comprising alumina modified by cerium, iii) mixing the support material with a solution comprising a vanadyl coordination complex or salt in a solvent to form loaded catalyst precursors, iv) reducing the loaded catalyst precursors with $H_2$ gas to form reduced catalyst precursors, and v) oxidizing the reduced catalyst precursors with oxygen to form the catalyst.

According to a third aspect, the present disclosure relates to a method for the oxidative cracking of an alkane to produce one or more olefins comprising flowing the alkane through a reactor comprising a catalyst chamber loaded with the catalyst of claim 1 at a temperature in the range of 450-700° C. to form the one or more olefins and a reduced catalyst.

In one embodiment, the reactor is a fluidized bed reactor and the oxidative cracking is performed in a gas phase oxygen free environment.

In one embodiment, the alkane is hexane the one or more olefins comprise at least one of ethylene, propylene, butylene, and mixtures thereof.

In one embodiment, the method further comprises further comprises i) oxidizing at least a portion of the reduced catalyst by flowing air through the catalyst chamber to regenerate the catalyst and ii) repeating the flowing and the oxidizing at least once with a less than 15% decrease in percent conversion of the alkane, a less than 15% decrease in selectivity for the one or more olefins relative to a total percentage of products formed, or both.

In one embodiment, the catalyst is present at an amount in the range of 0.50-2.5 g of catalyst per mL of alkane.

In one embodiment, the alkane is hexane and the method has a hexane conversion of 5-50 mol % at a reaction time of 1-40 seconds and a temperature of 500-650° C.

In one embodiment, the alkane is hexane and the method has a short olefins selectivity defined as moles of ethylene, propylene, and butylene produced per moles of hexane converted of 20-70% at a reaction time of 1-40 seconds and a temperature of 500-650° C.

In one embodiment, the alkane is hexane and the method has a $CO_x$ selectivity defined as moles of carbon monoxide and carbon dioxide produced per moles of hexane converted of no more than 50% at a reaction time of 1-40 seconds and a temperature of 500-650° C.

In one embodiment, the alkane is hexane and the method has a short olefins selectivity defined as moles of ethylene, propylene, and butylene produced per moles of hexane converted of at least 60% at a reaction time of 1-40 seconds and a temperature of 500-650° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
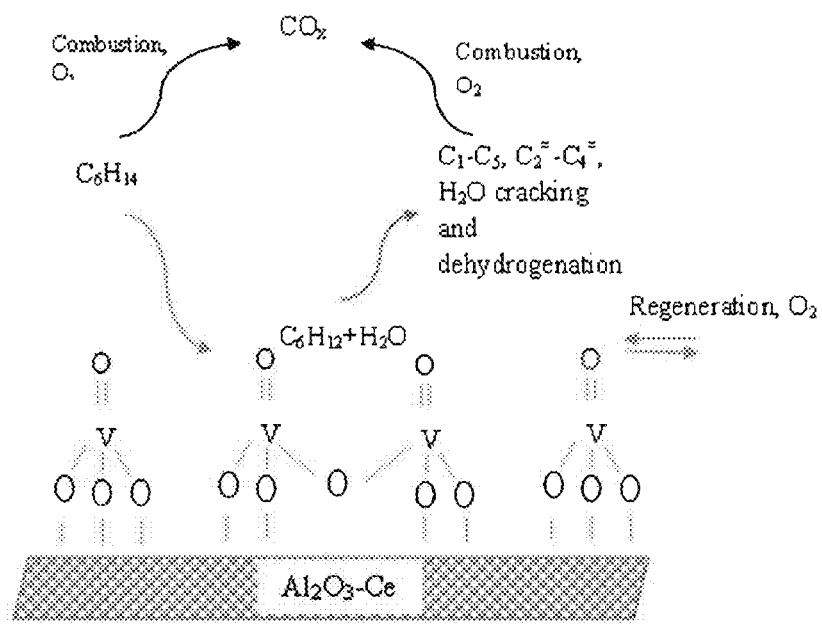
FIG. 1 is an exemplary schematic representation of the oxidative cracking reaction of hexane by the prepared $VO_x$/Ce-γ-$Al_2O_3$ catalyst sample in a gas phase oxygen free environment.

Referring now to the drawings. Embodiments of the present disclosure will now be described more fully hereinafter with reference to the accompanying drawings, in which some, but not all of the embodiments of the disclosure are shown.

According to a first aspect, the present disclosure relates to a catalyst, comprising i) a support material comprising alumina modified by cerium and ii) a catalytic material comprising one or more vanadium oxides disposed on the support material, wherein the catalyst comprises 1-15% of the one or more vanadium oxides by weight relative to the total weight of the catalyst.

Vanadium oxide (e.g., $V_2O_5$—vanadia) is considered to be one of the most important and useful metals to be used as a catalyst due to its physical and chemical properties, and catalysis is the most dominant non-metallurgical use of vanadia. The catalytic activity of vanadia is attributed to its reducible nature and its ability to easily change its oxidation state from $V^{+3}$ to $V^{+5}$. It is generally accepted that $V^{+5}$ is the highly active initial state of the catalyst in a cycle of oxidative dehydrogenation. Vanadium oxide catalysts have been used in many industrial and lab scale catalytic reactions and processes. In many cases, vanadia catalysts are doped with promoters to improve their activity or selectivity, while various supports are used to improve mechanical strength, thermal stability, longevity, and/or catalytic performance.

As used herein, a catalyst support material refers to material, usually a solid with a high surface area, to which a catalyst is affixed. The reactivity of heterogeneous catalyst and nanomaterial based catalysts occurs at the surface atoms. Thus, great effort is made herein to maximize the surface of a catalyst by distributing it over the support. The support may be inert or participate in the catalytic reactions. The support materials used in catalyst preparation play a role in determining the physical characteristics and performance of the catalysts. Typical supports include various kinds of carbon, alumina and silica. In a preferred embodiment, the dehydrogenation catalyst of the present disclosure comprises an alumina support material, preferably a cerium modified alumina support material.

As used herein, alumina refers to aluminum oxide, a chemical compound of aluminum and oxygen with the chemical formula $Al_2O_3$. Aluminum oxide is commonly called alumina and may also be referred to as aloxide, aloxite, or alundum. It is the most commonly occurring of several aluminum oxides and specifically identified as aluminum (III) oxide. It commonly occurs in its crystalline polymorphic phase $\alpha$-$Al_2O_3$ which composes the mineral corundum, the most thermodynamically stable form of aluminum oxide. $Al_2O_3$ is significant in its use to produce aluminum metals and noted for its high melting point. In one embodiment, the catalytic material is loaded on an inert alumina support. Exemplary inert alumina based inert materials include, but are not limited to aluminum oxide, alumina, alumina monohydrate, alumina trihydrate, alumina silica, bauxite, calcined aluminum hydroxides such as gibbsite, bayerite and boehmite as well as calcined hydrotalcite and the like.

In one embodiment, the alumina support material may be comprised of a plurality of different crystallographic phases. In the most common and thermodynamically stable form, corundum, the oxygen ions nearly form a hexagonal close-packed structure with aluminum ions filling two-thirds of the octahedral interstices. Each $Al^{3+}$ center is octahedral. In term of its crystallography, corundum adopts a trigonal Bravais lattice and its primitive cell contains two formula units of aluminum oxide. Aluminum oxide also exists in other phases, including the transition cubic $\gamma$ and $\eta$ phases, the monoclinic $\theta$ phase, the hexagonal $\chi$ phase, the orthorhombic $\kappa$ phase and the transition $\delta$ phase that can be tetragonal or orthorhombic. Each has unique crystal structure and properties. In the present disclosure, aluminum oxide or alumina may refer to $Al_2O_3$ having an $\alpha$ polymorph, a $\gamma$ polymorph, a $\eta$ polymorph, a $\theta$ polymorph, a $\chi$ polymorph, a $\kappa$ polymorph and a $\delta$ polymorph or mixtures thereof, preferably a $\gamma$ polymorph. In a preferred embodiment, the alumina of the present disclosure consists substantially of $\gamma$-$Al_2O_3$, preferably greater than 75% by weight relative to the total weight of alumina, preferably greater than 80%, preferably greater than 85%, preferably greater than 90%, preferably greater than 95%, preferably greater than 98%, preferably greater than 99% by weight relative to the total weight of the alumina. In at least one embodiment, the alumina support material consists essentially of $\gamma$-alumina ($\gamma$-$Al_2O_3$).

Alumina, especially $\gamma$-$Al_2O_3$ is used for its very high surface area on which active metal atoms/crystallites can spread out as reactive sites, but also for its enhancement of productivity and/or selectivity through metal-support interaction and spillover/reverse-spillover phenomena. In reactions, $\gamma$-$Al_2O_3$ must retain as much high surface area during reaction. Additives and/or modifiers and additional supports markedly increase the thermal stability of the support, effect acidity and active site metal support-interactions and prevent the loss of surface area under thermal reaction conditions.

In a preferred embodiment, the support material comprising alumina is modified by cerium metal. As used herein, cerium refers to the chemical element with symbol Ce and atomic number 58. Cerium is the most abundant of the rare earth elements or rare earth metals and is a soft silvery ductile metal belonging to the lanthanide group. Cerium has a variable electronic structure and four allotropic forms of cerium are known to exist at standard pressure. The high temperature form, $\delta$-cerium, has a bcc (body-centered cubic) crystal structure and exists above 726° C. The stable form below 726° C. to approximately room temperature is $\gamma$-cerium, with an fcc (face-centered cubic) crystal structure. The dhcp (double hexagonal close-packed) form of $\beta$-cerium is the equilibrium structure approximately from room temperature to −150° C. The fcc $\alpha$-cerium exists below about −150° C. Other solid phases occurring at high pressures also exist. Both $\gamma$ and $\beta$ forms are quite stable at room temperature, although the equilibrium transformation temperature is estimated at ~75° C. In the present disclosure, cerium may refer to Ce having an $\alpha$ polymorph, a $\gamma$ polymorph, a $\beta$ polymorph, and a $\delta$ polymorph or mixtures thereof, preferably a $\gamma$ or $\beta$ polymorph.

In a preferred embodiment, the catalyst of the present disclosure comprises 80-99% of alumina by weight relative to the total weight of the catalyst, preferably 82-98%, preferably 84-96%, preferably 86-95%, preferably 88-95% of alumina by weight relative to the total weight of the catalyst. In a preferred embodiment, the catalyst of the present disclosure comprises 0.05-1.0% of cerium by weight relative to the total weight of the catalyst, preferably 0.1-0.8%, preferably 0.15-0.6%, preferably 0.16-0.4%, preferably 0.18-0.3%, or about 0.2% of cerium by weight relative to the total weight of the catalyst. In a preferred embodiment, the catalyst of the present disclosure has a weight ratio of cerium to alumina in the range of 1:10000 to 1:100, preferably 1:8000 to 1:200, preferably 1:6000 to 1:400, preferably 1:4000 to 1:600, preferably 1:2000 to 1:800, preferably 1:1500 to 1:1000.

It is equally envisaged that the catalyst of the present disclosure may be adapted to incorporate additional rare earth metals. In some embodiments, these additional rare earth metals may be used in addition to, or in lieu of cerium. Exemplary additional rare earth metals include, but are not limited to, light rare earth elements (LREE such as Sc, La, Ce, Pr, Nd, Pm, Sm, Eu, and Gd; also known as the cerium group), and heavy rare earth elements (Y, Tb, Dy, Ho, Er, Tm, Yb, and Lu; also known as the yttrium group). It is equally envisaged that the catalyst of the present disclosure may be adapted to incorporate additional support materials and additional additives such as phase transformation stabilizers. In some embodiments, these additional support materials and additional additives may be used in addition to, or in lieu of alumina and/or cerium. Exemplary additional support materials include, but are not limited to oxides such as, $SiO_2$, $TiO_2$, $ZrO_2$, CeO, NbOs, MgO, CaO and zeolites. Exemplary additional thermal stabilizer additives include, but are not limited to, the elements La, Ce, Ba, Sr, Sm, Si, Pr and P. When lanthanum is used as an additive, the formation of lanthanum aluminate can decrease the surface energies of $\gamma$-$Al_2O_3$ lowering the driving force for sintering and stabilizing bulk phase transformation. In certain embodiments, the catalyst of the present disclosure comprises less than 5% of additional additives, such as elemental lanthanum, by weight relative to the total weight of the catalyst, preferably 0.1-3.0% of additional additives by weight relative to the total weight of the catalyst, preferably 0.5-2.0%, preferably 0.75-1.5%, preferably 0.8-1.1%, or about 1.0% of additional additives by weight relative to the total weight of the catalyst.

In a preferred embodiment, the catalyst of the present disclosure comprises a catalytic material disposed on the support material, wherein the catalytic material comprises one or more vanadium oxides. As used herein, "disposed on" or "impregnated" describes being completely or partially filled throughout, saturated, permeated and/or infused. The catalytic material may be affixed on one or more surfaces of the support material the catalytic material may be affixed on an outer surface of the support material or within pore spaces of the support material. The catalytic material may be affixed to the support material in any reasonable manner, such as physisorption or chemisorption and mixtures thereof. In one embodiment, greater than 10% of the surface area (i.e. surface and pore spaces) of the support material is covered by the catalytic material, preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99%. In preferred embodiments, the vanadium or vanadium oxide comprising catalytic material is homogeneously distributed or dispersed throughout the support material and on the surface of the support material. In preferred embodiments, this quality of the dispersion can be verified via scanning electron microscopy (SEM) and/or energy dispersive X-ray analysis (EDX) providing elemental mapping, preferably vanadium elemental mapping. In other embodiments the catalytic material may form localized clusters amongst the support material, form oxide species with the support catalyst or form layers of the catalytic material and vanadium species amongst the support material, or be heterogeneously disposed on the support material and its surfaces and mixtures thereof.

In a preferred embodiment, the catalytic material comprises one or more vanadium oxides. In terms of the present disclosure, vanadium oxide may refer to vanadium (II) oxide (vanadium monoxide, VO), vanadium (III) oxide (vanadium sesquioxide or trioxide, $V_2O_3$), vanadium (IV) oxide (vanadium dioxide, $VO_2$), vanadium (V) oxide (vanadium pentoxide, $V_2O_5$). Vanadium oxide may also refer to a vanadate, a compound containing on oxoanion of vanadium generally in its highest oxidation state of $^+5$. The simplest vanadate ion is the tetrahedral orthovanadate $VO_4^{3-}$ anion. Exemplary vanadate ions include, but are not limited to, $VO_4^{3-}$, $V_2O_7^{4-}$, $V_3O_9^{3-}$, $V_4O_{14}^{3-}$, $V_5O_{14}^{3-}$ and the like. In addition to these principal oxides of vanadium, various other distinct phases exist. Phases with the general formula $V_nO_{2n+1}$, wherein n is a whole number greater than zero exist between $V_2O_5$ (vanadium (V) species) and vanadium (IV) species. Examples of these phases include $V_3O_7$, $V_4O_9$ and $V_6O_{13}$. Phases with the general formula $V_nO_{2n+1}$, wherein n is a whole number greater than zero exist between vanadium (IV) species and $V_2O_3$ (vanadium (III) species). Termed Magneli phases, they are examples of crystallographic shear compounds based on rutile structure. Examples of Magneli phases include $V_4O_7$, $V_5O_9$, $V_6O_{11}$, $V_7O_{13}$ and $V_8O_{15}$. Many vanadium oxygen phases are non-stoichiometric. In a preferred embodiment, the catalyst of the present disclosure comprises 1-15% of the one or more vanadium oxides by weight relative to the total weight of the catalyst, preferably 2-14%, preferably 3-12%, preferably 3.5-10%, preferably 4-8%, preferably 4.5-6%, or about 5% of the one or more vanadium oxides by weight relative to the total weight of the catalyst.

In a preferred embodiment, the one or more vanadium oxides are of the formula $V_xO_y$, wherein x=1-4, preferably 1-3, more preferably 1-2 and y=2-10, preferably 2-5. In a preferred embodiment, the one or more vanadium oxides are at least one selected from the group consisting of $V_2O_5$, $VO_2$ and $V_2O_3$. $V_2O_5$ or vanadium (V) oxide or vanadium pentoxide is an inorganic compound that due to its high oxidation state is both an amphoteric oxide and an oxidizing agent. $V_2O_5$ is characterized by its valuable redox properties as $V_2O_5$ is easily reduced to the stable vanadium (IV) species. In certain embodiments, the catalyst comprises at least 50% of $V_2O_5$ by weight relative to the total weight of the one or more vanadium oxides, preferably greater than 60%, preferably greater than 70%, preferably greater than 80%, preferably greater than 85%, preferably greater than 90%, preferably greater than 95%, preferably greater than 96%, preferably greater than 97%, preferably greater than 98%, preferably greater than 99% of $V_2O_5$ by weight relative to the total weight of the one or more vanadium oxides, such as, for example 50-90% by weight $V_2O_5$, preferably 75-80% $V_2O_5$, more preferably 85-90% $V_2O_5$, even more preferably at least 90-95% $V_2O_5$, most preferably 95-99.9% $V_2O_5$ relative to the total weight of the one or more vanadium oxides. In certain embodiments, the catalyst of the present disclosure consists essentially of $V_2O_5$ and is substantially free of $V_2O_3$ and $VO_2$. In some embodiments, the catalyst of the present disclosure is substantially free of $V_2O_3$ and comprises a mixture of at least 50% $V_2O_5$ by weight relative to the total weight of the one or more vanadium oxides, with the balance substantially comprising $VO_2$.

The different vanadia phases that can be present in supported vanadia oxide catalysts as well as the distribution among the various vanadium oxide structures can depend on the synthesis method, the vanadium precursor, solvent, calcination temperature, vanadium oxide loading, oxide support, etc. At loadings below "monolayer coverage" isolated and oligomerized surface $VO_4$ species may be present on the oxide support. The surface $VO_4$ species may possess up to three different oxygen atoms including, but not limited to, oxygen atoms forming a vanadyl group (V=O), oxygen atoms bridging two vanadia atoms (V—O—V), and oxygen atoms bridging a vanadia atom and oxide support cation (V—O-support). Depending on the vanadia surface density as well as the support material, a vanadia "monolayer coverage" may be reached. A "monolayer" refers to a single, closely packed layer of atoms or molecules, here the one or more vanadium oxides. As used herein, "monolayer coverage" refers to the completion of a 2D surface of vanadium oxide overlayer on the alumina support, and the surface becomes saturated before 3D vanadium oxide and/or $V_2O_5$ crystallites start to form and grow subsequently. In certain preferred embodiments, the vanadium loading is below the monolayer coverage and the $VO_x$ species in the catalytic material are highly dispersed forming an amorphous phase on the $\gamma$-$Al_2O_3$ and Ce support surface. Alternatively, the monolayer coverage may be thought of as the minimum amount of single vanadium and/or vanadium oxide atoms or molecules to cover exactly 100% of the surface area (surface and pore spaces) of the support material uniformly. In a preferred embodiment, the monolayer coverage of the dehydrogenation catalyst of the present disclosure corresponds to 5-20 vanadium atoms per $nm^2$ of support, preferably 6-15 atoms/$nm^2$, preferably 7-10 atoms/$nm^2$, preferably 8-9 vanadium atoms per $nm^2$ of support. In certain embodiments, $V_2O_5$ crystallites may be present at vanadium oxide loadings below monolayer coverage when a precursor vanadium salt is not well dispersed over the support during synthesis or when a weak interaction exists between the vanadium oxide and the support. In certain preferred embodiments, the one or more vanadium oxides may form a crystalline phase on the surface of the cerium modified alumina support material, preferably a $V_2O_5$ crystalline phase. At high enough loadings, greater than monolayer coverage, vanadium oxide nanocrystals or nanoparticles having an average particle size of 1-100 nm, preferably 4-80 nm, preferably 10-60 nm, preferably 20-40 nm may be present on the surface of the catalyst support. In certain embodiments, the different surface vanadia species may be identified by techniques including, but not limited to, Raman spectroscopy, Fourier transform infrared spectroscopy (FT-IR), UV-vis spectroscopy, X-ray powder diffraction (XRD) and the like. In a preferred embodiment, the one or more vanadium oxides form an amorphous phase on the surface of the support material. In a preferred embodiment, the catalytic material comprising one or more vanadium oxides of the present disclosure forms a crystalline phase on the support surface. In other embodiments, the catalytic material may display an amorphous phase, a crystalline phase, or both in the form of a mixed amorphous and crystalline phase. In certain embodiments, the amorphous or non-crystalline form of the one or more vanadium oxide species may be favorable for olefin selectivity, in other embodiments the crystalline form of the one or more vanadium oxides may be favorable for $CO_2$ formation.

In certain embodiments, the catalytic material comprises one or more vanadium oxides and may optionally further comprise a promoter. As used herein, a promoter refers to an additive to improve catalyst performance. Metal promoters such as for example niobium may function to isolate active species (i.e. $VO_x$, more preferably $V_2O_5$) and to form secondary metallic oxides (i.e. $Nb_2O_5$) on support surface. Furthermore, the addition of promoters to the catalytic material blocks acid sites which decreases the total acidity of the catalyst. In certain embodiments, the decrease in acidity and increase in basicity may facilitate desorption of substrates from the catalyst surface, preventing further oxidation, such as, for example the undesirable combustion to carbon oxides ($CO_x$) in the oxidative dehydrogenation of alkanes or oxidative cracking of alkanes such as hexane. In a preferred embodiment, the catalyst of the present disclosure may further comprise 1.0-5.0% of promoter by weight relative to the total weight of the catalyst, preferably 1.5-4.0%, preferably 2.0-3.75%, preferably 3.0-3.5%, or about 3.25% of promoter by weight relative to the total weight of the catalyst. Exemplary promoters include, but are not limited to, metallic promoters (Nb, Cr, Mo, Ta, W), alkali promoters (Li, K, Rb) and halide promoters (Cl) and mixtures thereof. In preferred embodiments, the vanadium or vanadium oxide and promoter or promoters are homogeneously distributed throughout the catalyst support. In other embodiments the promoter may form localized clusters amongst the vanadium, form promoter oxide species with the support catalyst, form layers of promoter and vanadium species, or be disposed on the vanadium oxide species and mixtures thereof.

In a preferred embodiment, the present disclosure provides fluidizable catalysts for oxidative cracking and/or oxidative dehydrogenation (ODH) of alkanes preferably in reactors having a fluidized bed design. As used herein "fluidizable" refers to the ability to undergo fluidization which refers to a process similar to liquefaction whereby a granular material is converted from a static solid-like to a dynamic fluid-like state. The process occurs when a fluid (liquid or gas) is passed up through the granular material. A fluidized bed is formed when a quantity of a solid particulate substance is placed under appropriate conditions to cause a solid/fluid mixture to behave as a fluid. This is usually achieved by the introduction of pressurized fluid through the particulate medium. This results in the medium then having many properties and characteristics of normal fluids, such as the ability to free flow under gravity, or to be pumped using fluid type technologies. Fluidized bed types can be broadly classified by their flow behavior including, but not limited to, stationary or bubbling fluidized beds, circulating fluidized beds (CFB), vibratory fluidized beds, transport or flash reactor (FR), and annular fluidized beds (AFB).

In certain fluidized bed reactors, the catalyst pellets lie on a grate at the bottom of the reactor. Reactants are continuously pumped into the reactor through a distributor causing the bed to become fluidized. During the fluidization, the catalyst pellets are converted from a static solid like state to a dynamic fluid like state. The bed's behavior after initial fluidization depends on the state of the reactant. If it is a liquid the bed expands uniformly with an increased upward flow of the reactant, resulting in a homogeneous fluidization. If the reactant is a gas, the bed will be non-uniform because the gas forms bubbles in the bed, resulting in aggregative fluidization. In terms of the present disclosure, the fluidization may be homogeneous or aggregative. In certain embodiments, the reactant or feed is preferably an alkane including, but not limited to, ethane, propane, butane (including n-butane and isobutene), and hexane (including n-hexane, isohexanes, and neohexane) all of which may be present as gases and hence, an aggregative fluidization may be probable.

Properties and parameters for determining the fluidizability, reducibility, and oxygen carrying capacity of a catalyst can be both measured and calculated. The average particle size and the particle size distribution can be measured, for example, using a Mastersizer 2000 from Malvern Instruments. For spherical or substantially spherical catalyst particles, average particle size refers to the longest linear diameter of the catalyst particles. In a preferred embodiment, the catalyst of the present disclosure in any of its embodiments has an average particle size in the range of 20-160 µm, preferably 30-150 µm, preferably 40-120 µm, preferably 50-100 µm, more preferably 60-80 µm. In one embodiment, the particle size distribution of the catalyst of the present disclosure is 10-200 µm and greater than 75% of the particles have a particle size of 40-120 µm, preferably greater than 80%, preferably greater than 85%, more preferably greater than 90% have a particle size of 40-120 µm. In another embodiment, the catalyst of the present disclosure has a particle size distribution ranging from 33% of the average particle size to 133% of the average particle size, preferably 50-130%, preferably 60-125%, preferably 80-100%, preferably 90-110%, preferably 95-105% of the average particle size. In one embodiment, the catalyst particles of the present disclosure are monodisperse, having a coefficient of variation or relative standard deviation, expressed as a percentage and defined as the ratio of the particle size standard deviation ($\sigma$) to the particle mean size ($\mu$) multiplied by 100 of less than 25%, preferably less than 20%, preferably less than 15%, preferably less than 12%, preferably less than 10%, preferably less than 8%, preferably less than 6%, preferably less than 5%.

As used herein, the apparent particle density refers to the mass of the catalyst divided by the volume that it occupies. The apparent particle density can be assessed using a CREC-established method. In the method, a known amount of catalyst is introduced to a flask. The flask is filled with isopropanol and the apparent particle density (AD) is calculated using the following equation formula (I).

$$AD = \frac{W_{cat}}{V_T - V_{isopropanol}} \tag{I}$$

Where AD is the apparent particle density (g/cm³), $W_{cat}$ is the catalyst weight, $V_T$ is the flask volume and $V_{isopropanol}$ is the volume of isopropanol calculated as the ratio of the weight of isopropanol needed to fill the flask and the density of isopropanol. In a preferred embodiment, the catalyst of the present disclosure in any of its embodiments has an apparent particle density of 1.0-10.0 g/cm³, 1.1-5.0 g/cm³, preferably 1.25-4.0 g/cm³, preferably 1.5-3.5 g/cm³, more preferably 1.8-3.2 g/cm³.

In some embodiments, with the calculated average particle size and particle apparent density values, the fluidization regime of the catalyst particles of the present disclosure can be determined using Geldart's powder classification chart. Geldart groups powders into four "Geldart Groups" or "Geldart Classes". The groups are defined by solid-fluid density difference and particle size. Design methods for fluidized beds can be tailored based upon a particle's Geldart Group. For Geldart Group A the particle size is between 20 and 100 μm and the particle density is typically less than 1.4 g/cm³. Prior to the initiation of a bubbling bed phase, beds from these particles will expand by a factor of 2 to 3 at incipient fluidization, due to ta decreased bulk density. Most powder-catalyzed beds utilize this group. For Geldart Group B the particle size lies between 40 and 500 μm and the particle density is between 1.4-4 g/cm³. Bubbling typically forms directly at incipient fluidization. For Geldart Group C the group contains extremely fine and consequently the most cohesive particles. With a particle size of 20 to 30 μm, these particles fluidize under very difficult to achieve conditions, and may require the application of an external force, such as mechanical agitation. For Geldart Group D the particles in this regime are above 600 μm and typically have high particle densities. Fluidization of this group requires very high fluid energies and is typically associated with high levels of abrasion. Additionally, these particles are usually processed in shallow beds or in the spouting mode. The catalyst of the present disclosure is preferably fluidizable and may be classified as a Geldart Group A powder, a Geldart Group B powder, a Geldart Group C powder or a Geldart Group D powder, preferably as a Geldart Group B powder. In at least one preferred embodiment, the catalyst particles display a Geldart Group B powder property, which is highly fluidizable under oxidative cracking and ODH conditions. Large particles, such as those under Geldart Group D, may limit the gas phase reactant access to the inner layers of the catalyst. As a result, using smaller particles can minimize the diffusional resistance and reduction/oxidation rates can be maximized. On the other hand, very small particles, such as those under Geldart's Group C, can cause fluidization problems, channeling and loss of fines.

The Brunauer-Emmet-Teller (BET) theory aims to explain the physical adsorption of gas molecules on a solid surface and serves as the basis for an important analysis technique for the measurement of the specific surface area of a material. Specific surface area is a property of solids which is the total surface area of a material per unit of mass, solid or bulk volume, or cross sectional area. In a preferred embodiment, the catalyst of the present disclosure in any of its embodiments has a BET surface area in the range of 25-400 m²/g, preferably 50-350 m²/g, preferably 75-300 m²/g, preferably 100-250 m²/g, preferably 125-225 m²/g, preferably 150-200 m²/g.

The catalytic activity of many oxides in various processes is due to their Lewis and Bronsted acidities. In addition to effects on surface area, catalyst modifications (i.e. the modification of alumina with Ce) may also decrease the surface acidity and metal-support interactions of the catalyst, thereby enhancing olefin selectivity in oxidative cracking and oxidative dehydrogenation reactions and reducing coke ($CO_x$) formation. The catalyst acidity plays a role in metal support interactions that affect $VO_x$ reducibility. The reducibility may impact catalyst activity and selectivity by providing $O_2$ for oxidation and high acidity not favoring selective oxidation. A number of techniques have been developed for the characterization of acid-base surface properties of catalysts. The adsorption of volatile amines including, but not limited to, ammonia ($NH_3$), pyridine ($C_5H_5N$), n-butylamine ($CH_3CH_2CH_2CH_2NH_2$), quinolone ($C_9H_7N$) and the like is often used to determine the acid site concentration of solid catalysts. The amount of the base remaining on the surface after evacuation is considered chemisorbed and serves as a measure of the acid site concentration. The adsorbed base concentration as a function of evacuation temperature can give a site strength distribution. Another means of determining the site strength distribution is calorimetry or the temperature-programmed desorption (TPD).

Ammonia or $NH_3$-TPD experiments are used to determine the total acidity of the catalyst. TPD can further give an idea about metal-support interactions by modeling $NH_3$ desorption kinetics and be used to determine the strength of acid sites available on the catalyst surface. In a preferred embodiment, the catalyst of the present disclosure in any of its embodiments has a total acidity in the range of 4-16 mL of $NH_3$ per gram of catalyst, preferably 6-15 mL of $NH_3$ per gram of catalyst, preferably 8-14 mL of $NH_3$ per gram of catalyst, preferably 10-13 mL of $NH_3$ per gram of catalyst, or about 12 mL of $NH_3$ per gram of catalyst when measured with a heating rate of 5-20° C./min, preferably 10-15° C./min. In a preferred embodiment, the catalyst of the present disclosure has a lower acidity than pure alumina. In a preferred embodiment, the catalyst of the present disclosure has an energy of $NH_3$ desorption established by $NH_3$-TPD kinetic analysis and an indicator of active site metal-support interactions in the range of 1-20 kJ, preferably 2-15 kJ, preferably 4-10 kJ, preferably 5-8 kJ. In certain embodiments, the balance between the acidity and oxygen carrying capacity of the catalyst may play a role in the oxidative cracking of an alkane under gas phase oxygen free conditions. The acidity of the catalyst may favor cracking; however, excessive cracking produces undesired light/short paraffins (i.e. methane and/or ethane).

According to a second aspect, the present disclosure relates to a method for producing the catalyst of the present disclosure in any of its embodiments, comprising i) mixing an aluminum salt or hydrate with a cerium salt or hydrate in a solvent to form an alumina precursor solution, ii) adding a base to and hydrolyzing the alumina precursor solution to form the support material comprising alumina modified by cerium, iii) mixing the support material with a solution comprising a vanadyl coordination complex or salt in a solvent to form loaded catalyst precursors, iv) reducing the loaded catalyst precursors with $H_2$ gas to form reduced catalyst precursors, and v) oxidizing the reduced catalyst precursors with oxygen to form the catalyst.

Two main methods are typically used to prepare supported catalysts. In the impregnation method, the solid support or a suspension of the solid support is treated with a solution of a precatalyst (for instance a metal salt or metal coordination complex), and the resulting material then activated under conditions that will convert the precatalyst to a more active state, such as the metal itself or metal oxides of the metal. In such cases, the catalyst support is usually in the form of pellets or spheres. Alternatively, supported catalysts can be prepared from homogenous solution by co-precipitation. In terms of the present disclosure, it is envisaged that the catalyst may be formed by an impregnation method or a co-precipitation method, preferably by an impregnation method, preferably by an impregnation method through soaking with an excess solvent. Supports are usually thermally very stable and withstand processes required to activate precatalysts. For example, many precatalysts are activated by exposure to a stream of hydrogen or air (oxygen) at high temperatures, additionally many precatalysts may be activated and/or reactivated by oxidation-reduction cycles, again at high temperatures.

In one step of the process, an aluminum salt or hydrate is mixed with a cerium salt or hydrate in a solvent to form an alumina precursor solution. Exemplary aluminum salts or hydrates include, but are not limited to, aluminum sulfate, aluminum sulfate hydrate, aluminum chloride, aluminum chloride hydrate, aluminum hydroxide, aluminum hydroxide hydrate, aluminum nitrate, aluminum nitrate nonahydrate, and mixtures thereof. Preferably the aluminum salt or hydrate is aluminum nitrate nonahydrate ($Al(NO_3)_3 \cdot 9H_2O$). Exemplary cerium salts or hydrates include, but are not limited to, cerium sulfate hydrate, cerium sulfate, cerium acetylacetonate, cerium acetylacetonate hydrate, cerium acetate, cerium acetate hydrate, cerium carbonate, cerium carbonate hydrate, cerium oxalate, cerium oxalate hydrate, cerium nitrate hexahydrate, and mixtures thereof. Preferably the cerium salt or hydrate is cerium nitrate hexahydrate ($Ce(NO_3)_3 \cdot 6H_2O$). In a preferred embodiment, the solvent is polar protic solvent, preferably deionized water as the reaction medium. Exemplary additional polar protic solvents the may be used in addition to, or in lieu of deionized water include, but are not limited to, methanol, formic acid, n-butanol, isopropanol, n-propanol, ethanol, acetic acid. It is equally envisaged that the reaction may be adapted to be performed in a non-polar solvent (i.e. n-heptane, pentane, cyclopentane, hexane, cyclohexane, benzene, toluene, 1,4-dioxane, chloroform, diethyl ether, and dichloromethane), a polar aprotic solvent (dimethylformamide, tetrahydrofuran, ethyl acetate, acetone, acetonitrile, dimethyl sulfoxide, nitromethane, propylene carbonate), and mixtures thereof.

In a preferred embodiment, the aluminum salt or hydrate is aluminum nitrate nonahydrate ($Al(NO_3)_3 \cdot 9H_2O$), the cerium salt or hydrate is cerium nitrate hexahydrate ($Ce(NO_3)_3 \cdot 6H_2O$), and the solvent is deionized water. In a preferred embodiment the alumina precursor solution has an aluminum concentration of 0.5-5.0 M, preferably 0.75-4.0 M, preferably 1.0-3.0 M, preferably 1.5-2.5 M, or about 2.0 M. In a preferred embodiment, the weight ratio of the cerium salt or hydrate to the aluminum salt or hydrate is in the range of 1:10000 to 1:100, preferably 1:8000 to 1:200, preferably 1:6000 to 1:400, preferably 1:4000 to 1:600, preferably 1:2000 to 1:800, preferably 1:1500 to 1:1000.

In one step of the process, a base is added to hydrolyze the alumina precursor solution to form the support material comprising alumina modified by cerium. As used here in, hydrolysis refers to the cleavage of chemical bonds by the addition of water. Hydrolysis can be the reverse of a condensation reaction; hydrolysis adds water to break down. A common kind of hydrolysis occurs when a salt of a weak acid, a weak base, or both is dissolved in water which spontaneously ionizes into hydroxide anions and hydronium cations. Additionally, the salt dissociates into its constituent anions and cations. The base may be a strong base (i.e. lithium hydroxide, sodium hydroxide, potassium hydroxide, etc.) or a weak base (i.e. potassium carbonate, ammonium carbonate, ammonium hydroxide, sodium carbonate, calcium carbonate, sodium sulfate), preferably a weak base, most preferably ammonium carbonate (($NH_4)CO_3$). In a preferred embodiment the base has a concentration of 0.1-2.5 M, preferably 0.2-2.0 M, preferably 0.5-1.5 M, preferably 0.75-1.25 M, or about 1.0 M. Preferably, the base is added dropwise and the hydrolysis is performed at a temperature of 20-40° C., preferably 20-30° C., or about 25° C. for a period of less than 48 hours, preferably less than 36 hours, preferably less than 24 hours, preferably less than 18 hours, preferably less than 12 hours, preferably less than 8 hours, preferably less than 4 hours and optionally with vigorous stirring and/or ultrasonication to achieve a homogeneous mixture.

In a preferred embodiment, the obtained gel support material comprising alumina modified by cerium is dried before the dispersion of vanadium at 20-40° C., preferably 25-35° C. or about 30° C. for a period of up to 48 hours, preferably up to 36 hours, preferably up to 24 hours, and following natural drying at a temperature of up to 450° C., preferably up to 400° C., preferably up to 350° C., preferably up to 300° C., preferably up to 250° C., preferably up to 200° C., preferably up to 175° C., preferably up to 150° C., preferably up to 140° C., preferably up to 120° C., preferably up to 100° C. for a period of up to 60 hours, preferably up to 48 hours, preferably up to 36 hours, preferably up to 24 hours, preferably up to 12 hours, preferably up to 6 hours. In a most preferred embodiment, obtained gel support material comprising alumina modified by cerium is dried at 150° C. for 12 hours, subsequently at 200° C. for 12 hours, and finally calcined at 400° C. for 12 hours.

The manner in which the vanadium oxide is deposited onto a support can have an influence on the properties of the active component in the final catalyst. Typically the main method of dispersing vanadium oxide on support materials is the classic incipient wetness impregnation method in a solvent where the vanadium salt is soluble. The impregnation method is performed by contacting the support with a certain volume of solution containing the dissolved vanadium oxide precursor. If the volume of the solution is either equal to or less than the pore volume of the support, the technique is referred to as incipient wetness. This particular synthesis route can show a broad variation of vanadium oxide surface species at all loadings, particularly loadings below monolayer coverage, depending on the synthesis conditions. In one embodiment, this method may lead to the formation of crystalline three-dimensional $V_2O_5$ nanoparticles, even at low vanadium oxide loadings. In another embodiment, this method may lead to the formation of an amorphous vanadium oxide phase on the surface of the support.

In a preferred embodiment, the loaded catalyst precursors are prepared by an incipient wetness method of impregnation. The alumina-Ce support can be immersed in a solution comprising vanadium and/or a vanadium salt or coordination complex. In one embodiment, the vanadium salt or coordination complex may be a vanadium (IV), vanadium (V) or vanadium (III) salt. Exemplary vanadium salts or coordination complexes include, but are not limited to, ammonium metavanadate in mixtures of water and oxalic acid or methanol and oxalic acid, vanadium (III) acetylacetonate ($V(AcAc)_3$) or vanadyl acetylacetonate ($VO(AcAc)_2$) in toluene, $VO(iPrO)_3$, $VO(OC_2H_5)_3$, or $VO(OC_2H_7)_3$ in 2-propanol, as well as vanadyl sulfate, vanadium pentoxide, vanadium (III) chloride, vanadium oxytripropoxide, tetrakis(diethylamido)vanadium(IV), vanadium (IV) chloride, vanadium (III) chloride tetrahydrofuran complex, vanadium (V) oxychloride, vanadium (V)

oxyfluoride, and the like. Preferably, the vanadium salt or coordination complex is vanadium (III) acetylacetonate (V(AcAc)$_3$) or vanadyl acetylacetonate (VO(AcAc)$_2$), most preferably vanadyl acetylacetonate (VO(AcAc)$_2$). The vanadium salt is preferably phosphorous free. In a preferred embodiment, the solvent is a non-polar solvent. Exemplary non-polar solvents include, but are not limited to, pentane, cyclopentane, hexane, cyclohexane, benzene, toluene, 1,4-dioxane, chloroform, diethyl ether, dichloromethane and mixtures thereof, preferably the solvent is toluene. It is equally envisaged that the present method may be adapted to incorporate polar protic solvents including, but not limited to, formic acid, n-butanol, isopropanol, n-propanol, ethanol, methanol, acetic acid, and water, as well polar aprotic solvents including, but not limited to, tetrahydrofuran, ethyl acetate, acetone, dimethylformamide, acetonitrile, dimethyl sulfoxide, nitromethane, propylene carbonate and mixtures thereof.

In a preferred embodiment the vanadium salt is vanadyl acetylacetonate VO(AcAc)$_2$ and the solvent is toluene. In a preferred embodiment the solution has a vanadium concentration of 0.01-1.0 M, preferably 0.05-0.5 M, preferably 0.1-0.25 M, preferably 0.125-0.2 M, or about 0.15 M. In a preferred embodiment, the weight ratio of vanadyl coordination complex or salt to alumina modified by cerium support is in the range of 1:1 to 1:6, preferably 1:1.5 to 1:5, preferably 1:2 to 1:4, or about 1:3.5. In a preferred embodiment, the mixing of the alumina modified by cerium support material with the vanadyl coordination complex or salt in a solvent is performed at a temperature of 20-40° C., preferably 20-30° C., or about 25° C. for a period of less than 48 hours, preferably less than 36 hours, preferably less than 24 hours, preferably less than 18 hours, preferably less than 12 hours, preferably less than 10 hours, preferably less than 8 hours and optionally with stirring and/or ultrasonication to achieve a homogeneous mixture. In a preferred embodiment, the mixing is performed under vacuum conditions. After mixing the solution can be filtered and separated from the solvent to provided loaded catalyst precursors.

In another embodiment, it is equally envisaged that the method may be adapted to other means of dispersing and depositing the vanadium oxide on the support material. Both adsorption from solution (i.e. grafting) based on attaching vanadia from the solution through reaction with hydroxyl groups on the surface of the support and ion exchange methods permitting the ionic vanadium oxide species present in an aqueous solution to be electrostatically attracted by charged sites of the support surface have been used. Exemplary other means include, but are not limited to, vapor-fed flame synthesis, flame spray pyrolysis, sputter deposition, atomic layer deposition and chemical vapor deposition (CVD). For example, chemical vapor deposition (CVD) uses volatile molecular metal precursors (i.e. O=VCl$_3$, O=V(OC$_2$H$_5$)$_3$ or O=V(OiPr)$_3$) to modify oxide support surface and provide a way to control the dispersion of the active sites.

In certain embodiments, in addition to the methods employed to disperse vanadium oxide material on different supports, the drying and/or calcination used for the fixation of the vanadia may be a crucial step of the catalyst preparation due to the conversion of the initial vanadium species that may result in a broad variety of V$_x$O$_y$ species from a nominally simple impregnation process. At high calcination temperatures, mixed oxide compounds or solid solutions can be formed with some oxide supports (i.e. AlVO$_4$). In a preferred embodiment, the loaded catalyst supports or loaded catalyst precursors are dried before the reduction and the oxidation at room temperature for a period of up to 60 hours, preferably up to 48 hours, preferably up to 36 hours, preferably up to 24 hours, and following natural drying before the reduction and the oxidation at a temperature of up to 300° C., preferably up to 250° C., preferably up to 200° C., preferably up to 175° C., preferably up to 150° C., preferably up to 140° C., preferably up to 120° C., preferably up to 100° C. for a period of up to 60 hours, preferably up to 48 hours, preferably up to 36 hours, preferably up to 24 hours, preferably up to 12 hours, preferably up to 6 hours.

In one step of the process the loaded catalyst precursors are reduced with H$_2$ gas to form reduced catalyst precursors. As used herein, reduction refers to the gain of electrons or a decrease in oxidation state by a molecule, atom or ion. In a preferred embodiment, the loaded catalyst precursors are reduced under a flow of hydrogen gas comprising 1-40% H$_2$, preferably 2-20% H$_2$, preferably 4-18% H$_2$, preferably 6-16% H$_2$, preferably 8-14% H$_2$, or about 10% H$_2$ as a molar percentage and 60-99% helium or inert gas, preferably 70-95% helium, preferably 80-94% helium, preferably 85-92% helium, or about 90% helium as a molar percentage. Exemplary inert gases include nitrogen (N$_2$) and argon (Ar), preferably argon. In a preferred embodiment, the reduction under hydrogen gas flow is performed at a temperature of 300-800° C., preferably 400-780° C., preferably 500-760° C., preferably 600-750° C., or about 7500° C. for a period of 1-18 hours, preferably 2-12 hours, preferably 4-10 hours, or about 8 hours. In certain embodiments, the reduction of the loaded catalyst precursors may be performed in a fluidized bed reactor.

In one step of the process the reduced catalyst precursors are oxidized with oxygen to form the catalyst of the present disclosure in any of its embodiments. As used herein, oxidation refers to the loss of electrons or an increase in oxidation state by a molecule, atom or ion. Oxidation reactions are commonly associated with the formation of oxides from oxygen molecules. Oxygen itself is the most versatile oxidizer. In a preferred embodiment, the reduced catalyst precursors are oxidized under air flow comprising 20-25% O$_2$, preferably 20.5-22% O$_2$, or about 21% O$_2$ as a molar percentage and 75-80% N$_2$, preferably 77-79% N$_2$, or about 78% N$_2$ as a molar percentage. In a preferred embodiment, the oxidation under air flow or calcination under air flow is performed at a temperature of 300-800° C., preferably 400-780° C., preferably 500-760° C., preferably 600-7500° C., or about 7500° C. for a period of 1-18 hours, preferably 2-12 hours, preferably 4-10 hours, or about 8 hours.

According to a third aspect, the present disclosure relates to a method for the oxidative cracking of an alkane to produce one or more olefins comprising flowing the alkane through a reactor comprising a catalyst chamber loaded with the catalyst of the present disclosure in any of its embodiments at a temperature in the range of 450-700° C. to form the one or more olefins and a reduced catalyst.

The general nature of the alkane substrate is not viewed as particularly limiting to the oxidative cracking and/or oxidative dehydrogenation described herein. As used herein, "alkane" or "paraffin" unless otherwise specified refers to both branched and straight chain saturated primary, secondary and/or tertiary hydrocarbons of typically C$_1$-C$_{10}$. It is equally envisaged that the present disclosure may be adapted to cycloalkanes referring to cyclized alkanes containing one or more rings and substituted alkanes and/or substituted cycloalkanes referring to at least one hydrogen atom that is replaced with a non-hydrogen group, provided that normal valencies are maintained and that the substitution results in a stable compound. In a preferred embodiment, the alkane is at least one straight-chain linear alkane of $C_1$ to $C_{10}$, preferably $C_2$-$C_8$, more preferably $C_6$ selected from the group consisting of ethane ($C_2H_6$), propane ($C_3H_8$), butane ($C_4H_{10}$, n-butane, isobutane), pentane ($C_5H_{12}$, n-pentane, isopentane, neopentane), and hexane ($C_6H_{14}$, n-hexane, isohexane (2-methylpentane, 3-methylpentane, 2,3-dimethylbutane), neohexane) and the one or more olefin is a light olefin selected from the group consisting of ethylene, propylene, a butylene (1-butene, (Z)-but-2-ene, (E)-but-2-ene, isobutylene (2-methylpropene)) and butadiene respectively, more preferably the alkane is hexane, more preferably n-hexane and the one or more olefins comprise at least one of ethylene, propylene, butylene, and mixtures thereof. In certain embodiments, the alkane (i.e. n-hexane) may be sourced from other industrial processes such as those used in the petrochemical industry. Feedstocks generated from petroleum including, but not limited to, ethane, propane, butane, pentane, hexane, naphtha, pet naphtha, pygas, light pygas, and gas oil may serve as substrates for the method of oxidatively cracking an alkane described herein. In some embodiments, these streams or feedstocks may be processed (i.e. hydroprocessed) prior to the oxidative cracking and/or dehydrogenation. In certain embodiments, the alkane may be hexane and the hexane may be abundantly available from a natural gas source or a refinery off gas source.

As used herein, "cracking" is the process whereby complex organic molecules such as long chain hydrocarbons are broken down into simple molecules such as light hydrocarbons, by the breaking of carbon-carbon bonds in the precursors. The rate of cracking and the end products are strongly dependent on the temperature and presence of catalysts. Cracking is the breakdown of a large alkane into smaller and often more useful alkanes and alkenes. Simply, hydrocarbon cracking is the process of breaking a long-chain of hydrocarbons into short ones; the process may require high temperatures and high pressure. Oxidative cracking is considered a promising alternative to the existing thermal/steam/hydro cracking processes to produce olefins with advantages including, but not limited to, i) being an exothermic oxidation reaction, ii) being an adiabatic process, and iii) having less coke ($CO_x$) formation. The major challenges for large scale production of olefins via oxidative cracking of hydrocarbons include thermodynamic favorability of undesired products (lighter alkanes or paraffins by cracking) and complete oxidation of the reactant/products to $CO_x$ species. The lattice oxygen present in the catalyst of the present disclosure in any of its embodiments allows the cracking to proceed in an auto-thermal way, where the exothermic reaction provides heat for the cracking reaction. In this mechanism (FIG. 1) the lattice oxygen has multiple functions. First, the oxygen influences the radical gas-phase chemistry significantly due to the type and concentration of chain propagator radicals being greatly increased. At higher oxygen partial pressures the radical chemistry is only slightly influenced by the increasing oxygen concentration. Secondly, the oxygen facilitates the removal of hydrogen from the surface $OH^-$ species that are formed during the activation of alkane on the catalyst. The catalyst of the present disclosure is used for the oxidative cracking of an alkane, where the catalyst lattice oxygen is utilized for alkane activation. In addition, the catalyst has a relatively high acidity for the cracking reaction and simultaneously, dehydrogenation of alkanes to olefins takes place as shown in FIG. 1.

As used herein, dehydrogenation refers to a chemical reaction that involves the removal of hydrogen from a molecule. It is the reverse process of hydrogenation. The dehydrogenation reaction may be conducted on both industrial and laboratory scales. Essentially dehydrogenation converts saturated materials to unsaturated materials and dehydrogenation processes are used extensively in fine chemicals, oleochemicals, petrochemicals and detergents industries. The most relevant industrial pathway in light olefin production is typically steam cracking; the alternative fluid catalytic cracking (FCC) is only able to produce desired olefins in small concentrations with significant catalyst deactivation. The FCC catalytic dehydrogenation of alkanes is more selective but the reaction characteristics pose inherent difficulties and impose certain technical constraints. For example, thermal dehydrogenation is strongly endothermic and often requires operation at both high temperature and high alkane partial pressure. The oxidative dehydrogenation (ODH) of an alkane, which couples the endothermic dehydrogenation of the alkane with the strongly exothermic oxidation of hydrogen avoids the need for excess internal heat input and consumes hydrogen. The advantages of the alkane ODH reaction include, but are not limited to, that the reaction is i) exothermic, ii) thermodynamically unrestricted, iii) operates at a much lower temperature, and iv) minimizes coke ($CO_x$) deposition ensuring long-term stability of the catalyst.

Under standard operating conditions, an alkane is converted to one or more light olefins by oxidative cracking of and dehydrogenation in the presence of the catalyst described herein. The dehydrogenation proceeds in accordance with the chemical equation represented by formula (II), wherein y is a positive whole number, preferably y is 2, 3, or 4, and the alkane converted is ethane, propane, or butane and the corresponding olefin is ethylene, propylene, or butylene.

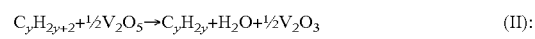
$$C_yH_{2y+2} + \tfrac{1}{2}V_2O_5 \rightarrow C_yH_{2y} + H_2O + \tfrac{1}{2}V_2O_3 \qquad (II)$$

In some embodiments the alkane to olefin conversion may be accompanied by complete oxidation of the alkane or the olefin as side and/or secondary reactions as represented in formula (III) and formula (IV), wherein y is a positive whole number, preferably y is 2, 3, or 4, more preferably y is 3, and y is the sum of a and b (y=a+b). The yield of alkenes or olefins obtained by oxidative dehydrogenation on catalysts is limited by alkene or alkane combustion to carbon oxides $CO_x$ (i.e. CO and $CO_2$). In some embodiments a=y and b=0 and $CO_2$ is the sole combustion product considered. The minimization of these undesirable consecutive and/or parallel combustion reactions is a key in the development of successful oxidative cracking and/or dehydrogenation catalysts. Additional undesirable side products include the light paraffins ($C_xH_{2x+2}$, wherein x<y). For example, if the alkane is hexane, desired products include light olefins (ethylene, propylene, butylene) and undesired products include $CO_x$ species (carbon monoxide, carbon dioxide) and C1-C5 paraffins (methane, ethane, propane, butane, pentane).

$$C_yH_{2y+2} + \tfrac{1}{2}V_2O_5 \rightarrow aCO_2 + bCO + \tfrac{(2y+2)}{2}H_2O + \tfrac{1}{2}V_2O_3 \qquad (III)$$

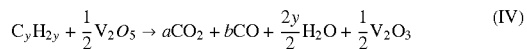
$$C_yH_{2y} + \tfrac{1}{2}V_2O_5 \rightarrow aCO_2 + bCO + \tfrac{2y}{2}H_2O + \tfrac{1}{2}V_2O_3 \qquad (IV)$$

The performance of the oxidative cracking and/or dehydrogenation can be modulated by adjusting conditions including, but not limited to, temperature, pressure, reaction time and/or catalyst loading. One important objective in developing oxidative cracking and/or dehydrogenation catalysts is to reduce the reaction temperature of the process to minimize energy consumption. In a preferred embodiment, the oxidative cracking of an alkane to one or more olefin is carried out a temperature in the range of 450-700° C., preferably 450-650° C., preferably 475-625° C., preferably 500-600° C., preferably 510-580° C., preferably 520-570° C., preferably 525-560° C., or about 550° C. and preferably at approximately standard pressure (100 kPa, 1 bar, 14.5 psi, 0.9869 atm) such as for example 10-20 psi, preferably 12-18 psi, preferably 14-16 psi, preferably 14.25-15 psi, or approximately 14.4-14.8 psi. In a preferred embodiment, the catalyst-alkane feed contact time is in the range of 1-60 seconds, preferably 1-40 seconds, preferably 2-35 seconds, more preferably 4-30 seconds, preferably 5-25 seconds, preferably 10-20 seconds or about 15 seconds. In a preferred embodiment, the catalyst loading or amount of catalyst present in the oxidative cracking and dehydrogenation reaction is in the range of 0.05-2.5 g of catalyst per mL of alkane feed injected, preferably 0.10-2.4 g/mL, preferably 0.5-2.35 g/mL, preferably 1.0-2.3 g/mL, preferably 1.5-2.25, preferably 1.75-2.2 g/mL, preferably 2.0-2.15 g of catalyst per mL of alkane feed injected, or about 2.125 g/mL. The conditions may vary from these ranges and still provide acceptable conditions for performing the oxidative cracking and/or dehydrogenation of an alkane to one or more olefins utilizing the catalyst of the present disclosure.

Oxidative cracking and/or dehydrogenation catalysts are evaluated for their percent conversion of the alkane as well as their selectivity to a product (i.e. light olefins (ethylene, propylene, butylene), light paraffins (methane, ethane, propane, butane, pentane) or $CO_x$ (CO and/or $CO_2$). The definitions used in calculating the conversion and selectivity are represented for the method of the present disclosure using the oxidative cracking catalyst are represented in formula (V) and formula (VI) respectively.

$$\text{Conversion of alkane} = \frac{\text{Moles of alkane converted}}{\text{Moles of alkane fed}} \times 100\% \quad \text{(V)}$$

$$\text{Selectivity to product } i = \frac{\text{Moles of product } i}{\text{Moles of alkane converted}} \times 100\% \quad \text{(VI)}$$

The conversion of alkane (i.e. hexane) (%) can be thought of as moles of alkane converted divided by moles of alkane fed multiplied by 100% and the selectivity (i.e. ethylene, propylene, and butylene) to product can be thought of as moles of product divided by the moles of alkane converted multiplied by 100%.

In one embodiment, the method of the present disclosure has an oxidative cracking and dehydrogenation alkane conversion rate as defined with formula (V) of up to 60%, preferably up to 55%, preferably up to 50%/o, preferably up to 45%, preferably up to 40%, preferably up to 35%, such as for example 5-50%, preferably 10-48%, preferably 15-45%, more preferably 20-40% and at least 5%, preferably at least 10%, preferably at least 15%, preferably at least 20%, preferably at least 25%. In another embodiment, the alkane is hexane and the method has an alkane conversion of up to 60%, preferably up to 55%, preferably up to 50%, preferably up to 45%, preferably up to 40%, preferably up to 35%, such as for example 5-50%, preferably 10-48%, preferably 15-45%, more preferably 20-40%. In a preferred embodiment, the alkane is hexane and the one or more olefins comprise ethylene, propylene and butylene and the method is performed with a catalyst-alkane feed contact time or reaction time of 1-40 seconds, preferably 2-35 seconds, more preferably 4-30 seconds, preferably 5-25 seconds, preferably 10-20 at a reaction temperature of 500-650° C., preferably 505-600° C., preferably 510-580° C., preferably 520-570° C., preferably 525-560° C. and the method has a hexane conversion of 5-50%, preferably 10-48%, preferably 15-45%, more preferably 20-40%.

In one embodiment, the method of the present disclosure has an oxidative cracking and dehydrogenation light/short olefin (ethylene, propylene, and butylene) selectivity relative to a total percentage of products formed as defined with formula (VI) of at least 20%, preferably at least 25%, preferably at least 30%, preferably at least 35%, preferably at least 40%, preferably at least 45%, preferably at least 50%, preferably at least 55%, preferably at least 60% such as for example 20-70%, preferably 30-65%, preferably 35-62%, more preferably 40-60%. In another embodiment, the alkane is hexane and the method has an light/short olefin (ethylene, propylene, and butylene) selectivity relative to a total percentage of products formed of at least 20%, preferably at least 25%, preferably at least 30%, preferably at least 35%, preferably at least 40%, preferably at least 45%, preferably at least 50%, preferably at least 55%, preferably at least 60% such as for example 20-70%, preferably 30-65%, preferably 35-62%, more preferably 40-60%. In a preferred embodiment, the alkane is hexane and the one or more olefins comprises light/short olefins (ethylene, propylene, and butylene) and the method is performed with a catalyst-alkane feed contact time or reaction time of 1-40 seconds, preferably 2-35 seconds, more preferably 4-30 seconds, preferably 5-25 seconds, preferably 10-20 at a reaction temperature of 500-650° C., preferably 505-600° C., preferably 510-580° C., preferably 520-570° C., preferably 525-560° C. and the method has a light/short olefins selectivity relative to a total percentage of products formed of at least 20%, preferably at least 25%, preferably at least 30%, preferably at least 35%, preferably at least 40%, preferably at least 45%, preferably at least 50%, preferably at least 55%, preferably at least 60% such as for example 20-70%, preferably 30-65%, preferably 35-62%, more preferably 40-60%.

In a more preferred embodiment, the alkane is hexane and the one or more olefins comprises light/short olefins (ethylene, propylene, and butylene) and the method is performed with a catalyst-alkane feed contact time or reaction time of 1-40 seconds, preferably 2-35 seconds, more preferably 4-30 seconds, preferably 5-25 seconds, preferably 10-20 at a reaction temperature of 500-650° C., preferably 505-600° C., preferably 510-580° C., preferably 520-570° C., preferably 525-560° C. and the method has a light/short olefins selectivity relative to a total percentage of products formed of at least 60%, preferably at least 62%, preferably at least 64%, preferably at least 66%, preferably at least 68%, preferably at least 70%, preferably at least 72%, preferably at least 75%, preferably at least 80% such as for example 60-80%, preferably 62-75%, preferably 64-72%, more preferably 66-70%.

In a preferred embodiment, the method of the present disclosure is performed with a catalyst-alkane, preferably hexane, feed contact time or reaction time of 1-40 seconds, preferably 2-35 seconds, more preferably 4-30 seconds, preferably 5-25 seconds, preferably 10-20 at a reaction temperature of 500-650° C., preferably 505-600° C., preferably 510-580° C., preferably 520-570° C., preferably 525-560° C. and the method has a $CO_x$ (carbon monoxide, carbon dioxide) or complete combustion selectivity relative to a total percentage of products formed that is less than the olefin selectivity, and the $CO_2$ selectivity is no more than 50%, preferably no more than 45%, preferably no more than 40%, preferably no more than 35%, preferably no more than 30%, preferably no more than 25%, preferably no more than 20%, preferably no more than 15%, preferably no more than 10% such as for example 5-40%, preferably 10-35%, preferably 20-30%.

In a preferred embodiment, the method of the present disclosure is performed with a catalyst-alkane, preferably hexane, feed contact time or reaction time of 1-40 seconds, preferably 2-35 seconds, more preferably 4-30 seconds, preferably 5-25 seconds, preferably 10-20 at a reaction temperature of 500-650° C., preferably 505-600° C., preferably 510-580° C., preferably 520-570° C., preferably 525-560° C. and the method has a light/short paraffins (methane, ethane, propane, butane, pentane) selectivity relative to a total percentage of products formed that is less than the olefin selectivity, and the light/short paraffins selectivity is no more than 50%, preferably no more than 45%, preferably no more than 40%, preferably no more than 35%, preferably no more than 30%, preferably no more than 25%, preferably no more than 20%, preferably no more than 15%, preferably no more than 10% such as for example 5-40%, preferably 10-35%, preferably 20-30%.

In a preferred embodiment, the method of the present disclosure and alkane oxidative cracking (OC) and/or alkane oxidative dehydrogenation (ODH) reactions incorporating the catalyst described herein are performed in a gas phase oxygen-free environment or atmosphere. The presence of excess oxygen inside the reactor or catalyst chamber increases the combustion reaction and therefore $CO_x$ production. Preferably, the amount of oxygen available for the reaction is controlled by the catalyst available, or lattice oxygen of the catalyst, specifically the vanadium oxide species. By this method, in reducing the catalyst loading or increasing the alkane feed to catalyst ratio one can further minimize the available oxygen and decrease the combustion reaction, thus enhancing light olefin selectivity.

In a preferred embodiment, the reactor is a fluidized bed reactor. As used herein, a fluidized bed reactor (FBR) is a type of reactor device that can be used to carry out a variety of multiphase chemical reactions. In this type of reactor, a fluid (gas or liquid) is passed through a granular solid material (usually a catalyst, preferably spherically shaped) at high enough velocities to suspend the solid and cause it to behave as though it were a fluid. This process, known as fluidization, imparts many important advantages to the fluidized bed reactor. It is equally envisaged that the method of the present disclosure may be adapted to be performed in a fixed-bed reactor, but this generally results in lower oxidative cracking catalyst activity.

The solid substrate (the catalytic material or catalyst of the present disclosure upon which the chemical species react) material in a fluidized bed reactor is typically supported by a porous plate known as a distributor, distributor plate or sparger distributor. The fluid is then forced through the distributor up through the solid material. At lower fluid velocities, the solids remain in place as the fluid passes through the voids in the material. This is referred to as a packed bed reactor. As the fluid velocity is increased, the reactor will reach a stage where the force of the fluid on the solids is enough to balance the weight of the solid material. This stage is referred to as incipient fluidization and occurs at this minimum fluidization velocity. Once this minimum velocity is surpassed, the contents of the reactor bed begin to expand and swirl around similar to an agitated tank or boiling pot of water. The reactor is now a fluidized bed. Depending on the operating conditions and properties of the solid phase various flow regimes can be observed in this type of reactor.

The fluidized bed reactor technology has many advantages including, but not limited to, uniform particle mixing, uniform temperature gradients and the ability to operate the reactor in continuous state. Due to the intrinsic fluid-like behavior of the solid material, fluidized beds do not experience poor mixing as in packed beds. The complete mixing allows for a uniform product that can often be hard to achieve in other reactor designs. The elimination of radial and axial concentration gradients also allows for better fluid-solid contact, which is essential for reaction efficiency and quality. Many chemical reactions require the addition or removal of heat. Local hot or cold spots within the reaction bed, often a problem in packed beds, are avoided in fluidized conditions such as the fluidized bed reactor. In other reactor types, these local temperature differences, especially hot spots, can result in product degradation. Thus fluidized bed reactors are well suited to exothermic reactions. The bed-to-surface heat transfer coefficients for fluidized bed reactors are also high. The fluidized bed nature of these reactors allows for the ability to continuously withdraw product and introduce new reactants into the reaction vessel. Operating at a continuous process state allows for the more efficient production and removes startup conditions in batch processes.

In certain embodiments, the fluidizability, reactivity, and stability of the catalyst of the present disclosure for experimental laboratory scale oxidative reactions and/or reaction behaviors may be demonstrated or evaluated in a Plexiglas unit with dimensions matching that of a CREC riser simulator. This type of reactor has a capacity of 50-60 $cm^3$, preferably 51-55 $cm^3$ or about 53 $cm^3$ and is a batch unit designed for catalyst evaluation and kinetic studies under fluidized bed reactor conditions. The major components of the CREC riser simulator include, but are not limited to, a vacuum box, a series of sampling valves, a timer, two pressure transducers and three temperature controllers. The product gas may be analyzed by gas chromatography (GC) with a thermal conductivity detector (TCD) and flame ionization detector (FID).

The oxidative cracking method of the present disclosure may be performed at various temperatures and contact times. In one embodiment, the contact times may be chosen to be consistent with catalyst reduction temperature reported by temperature programmed reduction (TPR) analysis. In a typical procedure, the oxidized catalyst sample of the present disclosure is loaded into the reactor basket and the reactor basket is checked for potential leaks. Following the leak test the system is purged by flowing pure inert gas, preferably nitrogen or argon, most preferably argon. The temperature program is started to heat the reactor to the desired temperature. The inert gas flow is maintained to keep the reactor from any interference of gas phase oxygen. Once the reactor reaches a desired temperature, the inert gas flow is discontinued and the reactor isolation valve is closed once a desired pressure level is reached. A vacuum pump may be used to evacuate the vacuum box down to less than 100 kPa, preferably less than 50 kPa, preferably less than 25 kPa, preferably less than 20 kPa. In one embodiment, the catalyst may be fluidized by rotating agitation, preferably by an impeller at a speed of 100-5000 rpm, preferably 1000-4500 rpm, preferably 2000-4250 rpm, preferably 3000-4000 rpm. In another embodiment, no agitation (i.e. 0 rpm) is necessary to fluidize the catalyst. The alkane feed is injected into the reactor using a preloaded gas tight syringe or other means and the reaction proceeds for a pre-specified amount of time. At the termination point, the isolation valve between the reactor and vacuum box may automatically open and transfer all reactant and products to the vacuum box for analysis.

In a preferred embodiment, the method for the oxidative cracking of an alkane to one or more olefins utilizing the catalyst of the present disclosure in any of its embodiments further comprises i) oxidizing at least a portion of the reduced catalyst by flowing air through the catalyst chamber to regenerate the catalyst of the present disclosure and ii) repeating the flowing and the oxidizing at least once with a less than 15% decrease in percent conversion of the alkane, a less than 15% decrease in selectivity for the one or more olefins relative to a total percentage of products formed, or both. In this manner, the catalyst can be recovered and reused in at least 2 reaction iterations, preferably at least 3, preferably at least 4, preferably at least 5, preferably at least 6, preferably at least 10, preferably at least 15, preferably at least 20 reaction iterations.

The catalyst of the present disclosure can be reformed or regenerated from the reduced catalyst; in this case the regeneration is the oxidation of the reduced vanadium species on the support surface. In a preferred embodiment, the regeneration is oxidation under air flow performed on the reduced catalyst and is performed at a temperature of up to 800° C., preferably up to 700° C., preferably up to 600° C., preferably up to 500° C., preferably up to 400° C. for a period of time of up to 3 hours, preferably up to 2 hours, preferably up to 1 hour, preferably up to 30 minutes, preferably up to 20 minutes, preferably up to 15 minutes, preferably up to 10 minutes, preferably up to 5 minutes. In a preferred embodiment, the regeneration of the catalyst may be performed in the catalyst chamber, without the need for flowing of the catalyst. In one embodiment, the reduced catalyst can flow out of the catalyst chamber to an additional chamber or re-oxidation chamber, be exposed to air flow to regenerate the catalyst, and flow back to catalyst chamber for use in subsequent reaction iterations. In a preferred embodiment, catalyst performance remains stable in cycles in terms of alkane conversion and light olefin (i.e. ethylene, propylene, butylene and mixtures thereof) selectivity indicating the catalyst's ability to be regenerated which confirms catalyst stability at high temperatures. In a preferred embodiment, at least a portion of the reduced catalyst is oxidized to regenerate the catalyst per reaction cycle, preferably up to 90%, preferably up to 80%, preferably up to 70%, preferably up to 60%, preferably up to 40%, preferably up to 30%, preferably up to 20%, preferably up to 15%, preferably up to 10% of the reduced catalyst is oxidized to regenerate the catalyst per reaction cycle.

In a preferred embodiment, there is a less than 10% change in percent alkane (i.e. hexane) conversion between the first and second iteration, preferably less than 5%, preferably less than 4%, preferably less than 3%, preferably less than 2%, preferably less than a 1% change in percent alkane conversion between the first and second iteration. In another embodiment, there is a less than a 20% change in percent alkane conversion, preferably less than 15%, preferably less than 10%, preferably less than 5%, preferably less than a 2% change in percent alkane conversion between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

In a preferred embodiment, there is a less than 10% change in percent $CO_x$ (i.e. carbon monoxide, carbon dioxide, and mixtures thereof) selectivity defined as moles of carbon monoxide and carbon dioxide produced per moles of alkane (i.e. hexane) converted, relative to a total percentage of products formed between the first and second iteration, preferably less than 5%, preferably less than 4%, preferably less than 3%, preferably less than 2%, preferably less than a 1% change in percent $CO_x$ selectivity relative to a total percentage of products formed between the first and second iteration. In another embodiment, there is a less than a 20% change in percent $CO_x$ selectivity relative to a total percentage of products formed, preferably less than 15%, preferably less than 10%, preferably less than 5%, preferably less than 2% change in percent $CO_x$ selectivity relative to a total percentage of products formed between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

In a preferred embodiment, there is a less than 10% change in percent light olefin (i.e. ethylene, propylene, butylene and mixtures thereof) selectivity defined as moles of ethylene, propylene and butylene produced per moles of alkane (i.e. hexane) converted, relative to a total percentage of products formed between the first and second iteration, preferably less than 5%, preferably less than 4%, preferably less than 3%, preferably less than 2%, preferably less than a 1% change in percent olefin selectivity relative to a total percentage of products formed between the first and second iteration. In another embodiment, there is a less than a 20% change in percent olefin selectivity relative to a total percentage of products formed, preferably less than 15%, preferably less than 10%, preferably less than 5%, preferably less than 2% change in percent olefin selectivity relative to a total percentage of products formed between the first and twentieth iteration, preferably between the first and fifteenth iteration, preferably between the first and tenth iteration, preferably between the first and fifth iteration, preferably between the first and fourth iteration, preferably between the first and third iteration, preferably between the first and second iteration.

The examples below are intended to further illustrate methods protocols for preparing and characterizing the catalysts of the present disclosure. Further, they are intended to illustrate assessing the properties and performance of these catalysts. They are not intended to limit the scope of the claims.

EXAMPLE 1

Catalyst Synthesis

Aluminum nitrate nona-hydrate, cerium nitrate hexa-hydrate and vanadium acetylacetonate were obtained from Sigma-Aldrich and used without further purification. Ammonium carbonate was purchased from Fisher Limited and deionized water was used in the preparations of the chemicals. The cerium doped mesoporous γ-$Al_2O_3$ support was prepared by modifying the approaches previously presented by X. Shang, et al. and J. Wang, et al. [X. Shang, X. Wang, W. Nie, X. Guo, X. Zou, W. Ding, and X. Lu, "Facile strategy for synthesis of mesoporous crystalline γ-alumina by partially hydrolyzing aluminum nitrate solution," *J. Mater. Chem.*, vol. 22, no. 45, p. 23806, 2012; and J. Wang, K. Shang, Y. Guo, and W. C. Li, "Easy hydrothermal synthesis of external mesoporous γ-Al$_2$O$_3$ nanorods as excellent supports for Au nanoparticles in CO oxidation," *Microporous Mesoporous Mater.*, vol. 181, no. 3, pp. 141-145, 2013.—each incorporated herein by reference in its entirety]. A surfactant free approach was used and Ce(NO$_3$)$_3$.6H$_2$O was added to an Al-precursor solution which was then partially hydrolyzed by ammonium carbonate and subsequently calcined at 400° C. The crystalline Ce-γ-Al$_2$O$_3$ was thus obtained, exhibiting a higher BET surface are, a uniform pore size distribution, and a better thermal stability. In this manner, Al(NO$_3$)$_3$.9H$_2$O (37.5 g) was dissolved in deionized water (50 mL), and the appropriate amount of Ce(NO$_3$)$_3$.6H$_2$O was added to the Al-precursor solution. Subsequently, (NH$_4$)$_2$CO$_3$ (1 molar) was added dropwise to the Al-precursor solution under vigorous stirring, the calcination temperature was set at 400° C. for 6 hours. The mixture was then partially hydrolyzed by one molar ammonium carbonate solution until the formation of white precipitates was observed. The obtained gel was dried in a oven at 30° C. for 24 hours, and then aged at 150° C. and 200° C. each for a 12 hour interval at a ramping rate of 1° C./min and finally calcined at 400° C. for 12 hours at a ramping rate of 1° C./min.

Vanadium was dispersed on the Ce-γ-Al$_2$O$_3$ using an excessive solvent impregnation method under vacuum conditions. The VO$_x$/Ce-γ-Al$_2$O$_3$ synthesis method involves five steps: i) active site wet impregnation, ii) filtration, iii) drying, iv) reduction, and v) calcination. The vanadium content was kept constant at 5 wt % by dissolving 0.86 g of vanadium acetylacetonate in an excess amount of toluene. The resultant vanadium precursor solution was added dropwise to 3 g of Ce-γ-Al$_2$O$_3$ solid support under vigorous stirring conditions. The solution was stirred for 6 hours under vacuum and then filtered. After the filtration the solid residue was allowed to dry at room temperature for 24 hours and then further dried in an oven at 140° C. at a ramping rate of 0.5° C./min for an additional 6 hours. Upon drying the prepared material was reduced in a fluidizable bed reactor. The source of fluidization and reduction was a 10% H$_2$ with He gas mixture. The bed temperature of the dried catalyst was raised from the ambient to 750° C. at a ramping rate of 0.5° C./min and held constant at 750° C. for an additional 8 hours. Upon completion of the reduction step, the catalyst was oxidized in an oven at 750° C. using the same ramping rate and time interval employed for the reduction step.

EXAMPLE 2

X-Ray Diffraction (XRD) Analysis and Characterization of the Prepared Catalyst

The physio-chemical make-up of the different crystalline phases of the catalyst were studied by X-ray diffraction (XRD) analysis. The analysis was conducted using a Rigaku Mini-Flex II bench top XRD diffractometer. Cu—Kα monochromatic radiation (λ=0.15406 nm, 30 kV, 15 mA) over a 10-90° range at a scan rate of 3°/min and with the step size of 0.02 was used to analyze the diffraction pattern of the prepared catalyst and supports.

Figure 2:
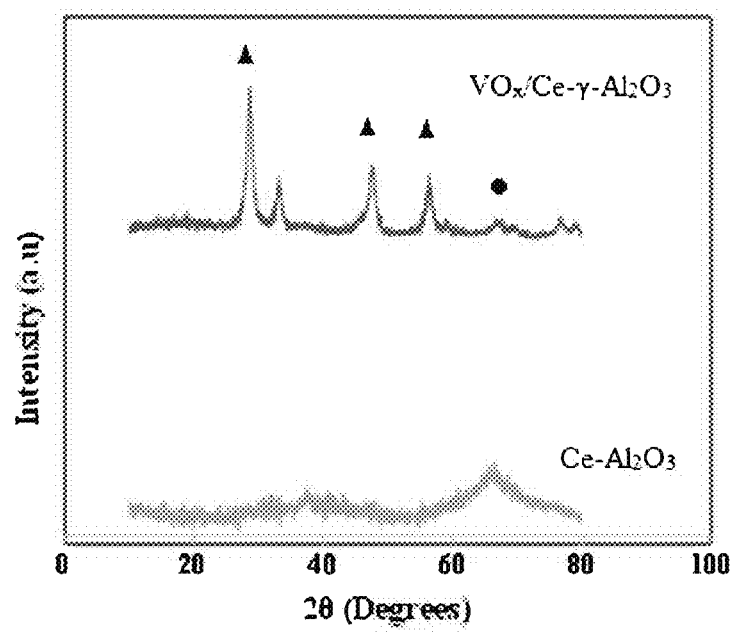
FIG. 2 is the X-ray diffraction (XRD) patters of the prepared $VO_x$/Ce-γ-$Al_2O_3$ catalyst sample and the Ce-γ-$Al_2O_3$ support.

FIG. 2 presents the XRD patterns of the (a) VO$_x$/Ce-γ-Al$_2$O$_3$ and (b) Ce—Al$_2$O$_3$ support samples. As can be seen, γ-Al$_2$O$_3$ peaks appear at 45° and 67° in both Ce-γ-Al$_2$O$_3$ support and VO$_x$/Ce-γ-Al$_2$O$_3$ patterns [S. A. Al-ghamdi, M. M. Hossain, and H. I. De Lasa, "Kinetic Modeling of Ethane Oxidative Dehydrogenation over VO$_x$/Al2O3 Catalyst in a Fluidized-Bed Riser Simulator," 2013; and I. E. Wachs and B. M. Weckhuysen, "Structure and reactivity of surface vanadium oxide species on oxide supports," *Appl. Catal. A Gen.*, vol. 157, pp. 67-90, 1997.—each incorporated herein by reference in its entirety]. VO$_x$ species including isolated and crystalline vanadia are present on the support surface. Peaks which appear at 30° and 37° are relevant to the crystalline VO$_x$ phase, which is not favorable for the selectivity of the cracking reaction. This phase can be accounted for by formation of the V—O—V bond and appears at high vanadium loading and at high support acidity [F. Klose, "Selective oxidation of ethane over a VO$_x$/γ-Al$_2$O$_3$ catalyst—investigation of the reaction network," *Appl. Catal. A Gen.*, vol. 260, no. 1, pp. 101-110, March 2004.—incorporated herein by reference in its entirety]. The absence of VO$_x$ peaks in the range of 5° to 20° is related to either the formation of a highly dispersed amorphous phase of VO$_x$ or formation of very small crystals of VO$_x$ which are undetectable by the XRD analysis [I. A. Bakare, S. A. Mohamed, S. Al-Ghamdi, S. A. Razzak, M. M. Hossain, and H. I. de Lasa, "Fluidized bed ODH of ethane to ethylene over VOx-MoOx/γ-Al$_2$O$_3$ catalyst: Desorption kinetics and catalytic activity," *Chem. Eng. J.*, 2014.—incorporated herein by reference in its entirety]. Consequently, the amorphous VO$_x$ phase indicates good dispersion of VO$_x$ species on the support surface, which results in controlled oxygen release during oxidative cracking and thus a lower combustion and a higher selectivity to olefins. Furthermore, the VO$_x$/Ce-γ-Al$_2$O$_3$ catalyst with 0.2 wt % Ce content of dopant shows no peaks for CeO$_2$ and it also the peaks of the support structure which is due to the presence of the Ce-γ-Al$_2$O$_3$ support.

EXAMPLE 3

Fourier Transform Infrared (FTIR) Spectroscopy Analysis and Characterization of the Prepared Catalyst Fourier transform infrared (FTIR) spectra of the prepared samples were collected using a Nicolet 6700 Thermo Fisher Scientific instrument. For each experimental run, 3 mg of the catalyst was thoroughly mixed with 400 mg of standard KBr. The excited FTIR spectra were collected over the range of 400-4000 cm$^{-1}$.

Figure 3:
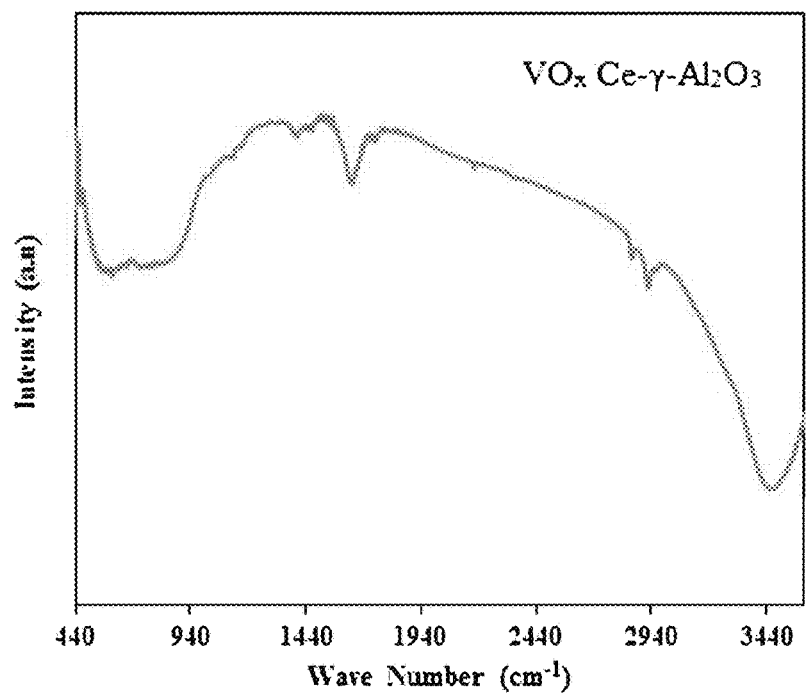
FIG. 3 is the Fourier transform infrared (FTIR) absorption spectra of the prepared $VO_x$/Ce-γ-$Al_2O_3$ catalyst sample.

FIG. 3 presents the FTIR spectra of the VO$_x$/Ce-γ-Al$_2$O$_3$ catalyst sample which shows a broad spectral band between the wavenumber 3000-3800 cm$^{-1}$. The band at 1650 cm$^{-1}$ corresponds to the O—H stretching frequency due to adsorbed water or a surface hydroxyl group. In addition, the band at 934 cm$^{-1}$ is relevant to Al—O—V vibrations and is due to significant interaction γ-Al$_2$O$_3$ which confirms the presence of isolated VO$_x$ species on the surface of the support in agreement with the XRD patterns [A. M. Elfadly, A. M. Badawi, F. Z. Yehia, Y. A. Mohamed, M. A. Betiha, and A. M. Rabie, "Selective nano alumina supported vanadium oxide catalysts for oxidative dehydrogenation of ethylbenzene to styrene using CO2 as soft oxidant," *Egypt. J. Pet.*, vol. 22, no. 3, pp. 373-380, December 2013.—incorporated herein by reference in its entirety]. Furthermore, the peaks at 1052 cm$^{-1}$ and 1100 cm$^{-1}$ are related to the V=O stretching mode and the vibration at 754 cm$^{-1}$ and 1100 cm$^{-1}$ can be attributed to the V—O—V bond, which indicates the presence of the VO$_x$ crystal phase. Ce—O bond vibrations are reported to be in the range of 440-500 cm$^{-1}$. Thus, the FTIR spectra confirms the presence of isolated and crystalline VO$_x$ species on the support surface; however, these small crystals of VO$_x$ and Ce—O species have not been detected by XRD.

EXAMPLE 4

Laser Raman Spectroscopy Analysis and Characterization of the Prepared Catalyst Raman spectra were collected using Yvon Jobin equipment using a cooled iHR 320 Horiba spectrometer with a CCD detector, which removes the elastic laser scattering. The laser source was green type at 532 nm and the laser intensity was 50% at a spectrum window of 50 to 2500. A powder form of the catalyst sample was used to minimize the possibility of mass transfer limitations and to ensure that all catalyst particles in the cell are exposed to the flowing gases.

Figure 4:
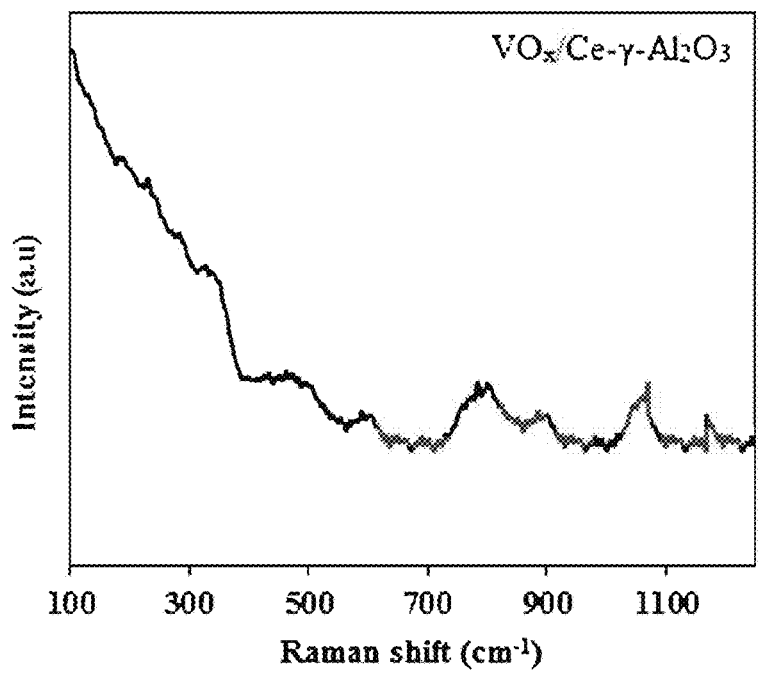
FIG. 4 is the laser Raman spectroscopy spectra of the prepared $VO_x$/Ce-γ-$Al_2O_3$ catalyst sample.

Raman spectroscopy was used to investigate the nature of the vanadium oxides on the support surface. FIG. 4 shows the Raman spectra of the catalyst sample. The appearance of the $VO_x$ peaks depends on the vanadium loading and on the surface concentration of the $VO_x$ species. Peaks in the range of 200 to 600 cm$^{-1}$ are from the vibration of poly-vanadate and crystalline $V_2O_5$ which results from the V—O—V bond at high vanadium loading. Additionally, peaks at 995 and 1130 cm$^{-1}$ are relevant to the V═O bond which form isolated $VO_x$ species.

The Raman analysis is in agreement with the FTIR results since analyses confirm the presence of isolated, poly-vanadate and crystalline $VO_x$ on the support surface. However, previously published literature reports that poly-vanadate and crystalline $VO_x$ are formed in small amounts in comparison with isolated $VO_x$ species at low vanadium loading and with good dispersion. In addition, the formation of a surface vanadium oxide layer on oxide supports is more favorable than crystalline $V_2O_5$ due to the surface mobility of vanadium oxide and the lower free surface energy of crystalline $V_2O_5$ (9-8×10$^{-6}$ J cm$^{-2}$) relative to supports ($Al_2O_3$~68-70×10$^{-6}$ J cm$^{-2}$; $ZrO_2$~59-80×10$^{-6}$ J cm$^{-2}$; $TiO_2$~28-38×10$^{-6}$ J cm$^{-2}$).

EXAMPLE 5

Temperature Programmed Reduction-Oxidation (TPR/TPO) Characterization of the Prepared Catalyst's Reducibility and Stability The reducibility and reduction temperature of the oxide catalyst was determined by using the temperature programmed reduction (TPR) analysis. The TPR experiments were carried out on Micrometrics AutoChem II 2920 analyzer. For a typical TPR analysis, approximately 200 mg of the fresh catalyst sample was loaded in a quartz U-tube, then the sample was heated to 300° C. for 3 hours in an argon (50 mL/min) environment. After cooling to 30° C. in argon (Ar) the reduction was carried out using a reducing gas mixture of 90 vol % Ar and 10 vol % $H_2$, which was heated at the constant rate of 10° C./min (50 mL/min) up to 900° C. and was maintained for 1 hour at 900° C. The $H_2$ consumption by the oxide catalyst is recorded using a calibrated thermal conductivity detector (TCD) that measures the change in the concentration of the $H_2$ in the outlet stream.

Catalyst activity has been measured using TPR analysis. Activity has been measured in terms of $H_2$ consumption, which gives an indication about the catalyst activity in the oxidative dehydrogenation (ODH) reaction and the oxygen carrying capacity. Catalyst activity in TPR/TPO cycles is similar to reaction/regeneration of the catalysts as expected during the actual ODH reaction with ethane. Formula (VII) gives the equation of the TPR reaction and formula (II) gives the equation of the gas phase oxygen free ODH reaction.

$$V_2O_5 + 2H_2 \rightarrow V_2O_3 + 2H_2O \tag{VII}$$

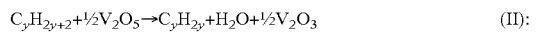
(II):

In can be seen that in both the TPR reaction (formula (VII)) and the ODH reaction (formula (II)) $V_2O_5$ is reduced to $V_2O_3$. In contrast, the TPO cycle (formula (VIII)) represents the catalyst regeneration cycle following the reduction in the TPR reaction. Formula (VIII) gives the equation of the TPO reaction.

$$V_2O_3 + O_2 \rightarrow V_2O_5 \tag{VIII}$$

Figure 5:
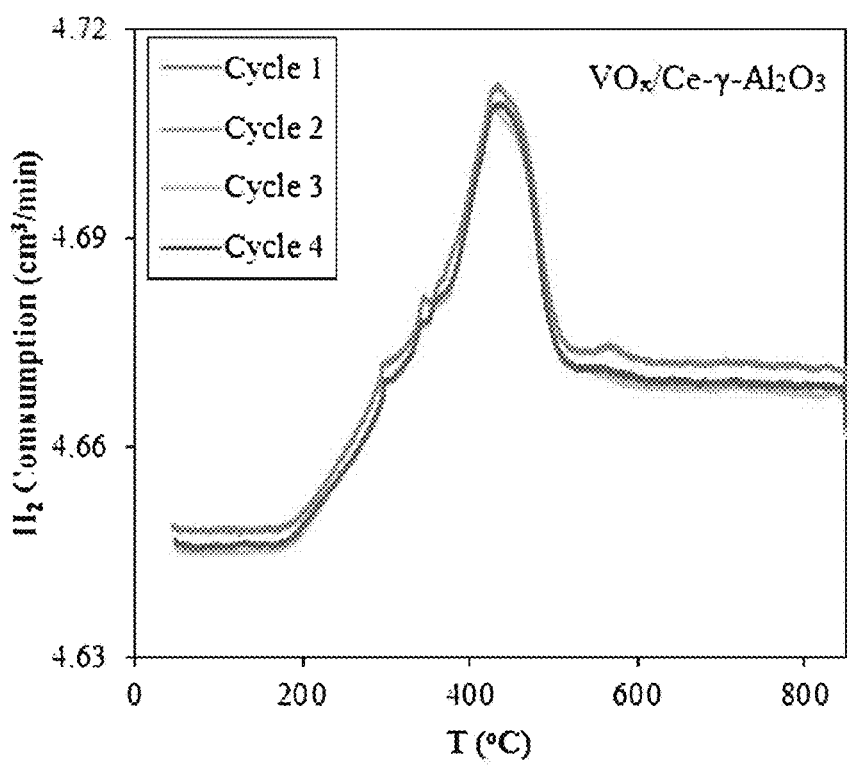
FIG. 5 is the temperature programmed reduction-oxidation (TPR/TPO) profiles of the prepared $VO_x$/Ce-γ-$Al_2O_3$ catalyst sample over multiple cycles.

FIG. 5 presents the TPR profile of the $VO_x$/Ce-γ-$Al_2O$ catalyst. Furthermore, $H_2$ consumption was calculated from the TPR profile by calculating the area under the curve. It was established that the oxide phase is responsible for the overall catalytic activity and selectivity in oxidative dehydrogenation, which increase olefin production in the oxidative cracking reaction. However, the crystalline $VO_x$ phase only has a small contribution to the catalyst and a minor effect on the catalytic activity and selectivity. Moreover, the single peak in the TPR profile indicates that the $V_2O_5$ reduction occurs in one step, as in formula (VII).

FIG. 5 additionally shows that catalyst stability has been tested using repeated TPR/TPO cycles. Repeated TPR/TPO cycles give an indication regarding catalyst thermal stability and help evaluate alumina phase change at high temperature as well as the catalysts ability for regeneration (re-oxidization). FIG. 5 shows consistent cycles demonstrating good catalyst stability at high temperatures up to 800° C. With regards to the mechanisms of phase transformation of vanadia species, it is reported that these species usually form during the reduction steps, which create oxygen vacancies at the surface. When the concentration of the oxygen vacancies surpasses a certain critical value, the vacancies aggregate into a vacancy disc, called a shear plane. Part of vanadium oxide may shear so that along the shear plane the linkage between trigonal bipyramids is changed from corner-sharing into edge-sharing. Thus, another stable structure is formed, which is stoichiometrically different from the original structure [Y. H. Kim and H. Lee, "Redox Property of Vanadium Oxide and Its Behavior in Catalytic Oxidation," vol. 20, no. 12, 1999.—incorporated herein by reference in its entirety].

$H_2$ consumption was further utilized to calculate the reducible vanadium amount in the catalyst samples. The percentage of vanadium oxide reduction (oxygen carrying capacity) was calculated using the relation of formula (IX) and formula (X).

$$\text{fraction reduced \%} = \frac{W_V}{W_0} \times 100\% \tag{IX}$$

$$W_V = \frac{MW_V \times V_{H_2}}{v \times V_g} \tag{X}$$

In this formula, (1) $W_V$ is the amount of reduced vanadium (g), (2) $MW_V$ is the molecular weight of vanadium (g/mol), (3) $V_{H_2}$ is the volume of reacted hydrogen (cm$^3$ at STP), (4) $V_g$ is the molar volume of gas (cm$^3$/mol at STP), (5) $W_0$ is the initial weight of vanadium (g) and (6) v is the stoichiometric number of hydrogen based on the reaction stoichiometry presented in formula (VII). Assuming that $V_2O_5$ is the initial reducible catalyst species on the support, then the reduction reaction equation of formula (VII) applies. Table 1 shows that over the repeated TPR/TPO cycles, the percentage of total $VO_x$ species reduction was found to be 78-79%. Thus, only approximately 22% of the loaded vanadium is not reducible. These findings agree with the FTIR and Raman results, which confirm the presence of isolated and crystalline $VO_x$ species, and as previously described, crystalline $VO_x$ species do not contribute to the ODH reaction.

TABLE 1

Reduced vanadium over repeated TPR/TPO cycles (catalyst weight = 0.1 g)

| Cycle | Total $H_2$ consumption ($cm^3/g_{catalyst}$) | Reduced vanadium (wt %) |
|---|---|---|
| 1 | 35 | 81.0 |
| 2 | 34.5 | 79.9 |
| 3 | 33.9 | 78.5 |
| 4 | 33.7 | 78.0 |

EXAMPLE 6

$NH_3$-Temperature Programmed Desorption ($NH_3$-TPD) Characterization of the Prepared Catalyst's Acidity The temperature programmed desorption (TPD) experiments were carried out on the same equipment as the TPR analysis. For each experimental run, approximately 200 mg of the catalyst sample is placed over quartz wool in a quartz U-tube. In a typical procedure, the quartz tube containing the catalyst is first evacuated under a helium flow rate of 30 mL/min for 2 hours at 300° C. and then cooled to 100° C. Subsequently, the samples were saturated with a 4.55% $NH_3$/He gas mixture at a rate of 50 mL/min for 1 hour. The samples were then flushed with the helium (50 mL/min) for 1 hour to remove the physically adsorbed $NH_3$. The TPD analysis of the ammonia saturated samples was carried out from 100° C. to 750° C. at the heating rate of 10° C./min. The exit concentration of the desorbed gases was analyzed by the thermal conductivity detector.

Figure 6:
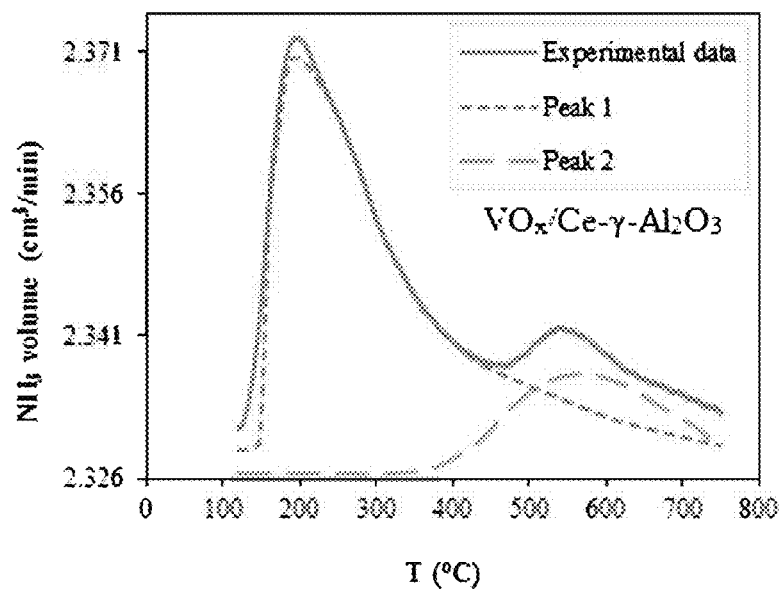
FIG. 6 is the ammonia temperature programmed desorption ($NH_3$-TPD) profile of the prepared $VO_x$/Ce-γ-$Al_2O_3$ catalyst sample with temperature rising gradually with a constant value β=10° C./min and deconvolution peaks.

Catalyst total acidity plays a vital role in the reaction of cracking hexane. It is important to optimize catalyst acidity to achieve a high conversion, while at the same time avoiding severe cracking which produces methane. Catalyst acidity was estimated using $NH_3$-TPD analysis using 0.1 g of the $VO_x/Ce$-$\gamma$-$Al_2O_3$ catalyst sample. FIG. 6 shows $NH_3$ desorption in the temperature range from 120 to 750° C. It can be seen that $NH_3$ disported at low and high temperatures which indicates the presence of strong acid sites. The total volume of desorbed ammonia was estimated by calculating the area under the curve of the experimental data, and found to be 12.2 $cm^3$ $NH_3$/g of catalyst, which is higher than comparative exemplary catalysts $VO_x/c$-$Al_2O_3$ and $VO_x$—$MoO_x/\gamma$-$Al_2O_3$ that do not show desorption at high temperature. In addition, peaks have been de-convoluted in order to determine the volume of ammonia desorbed from weak and strong acid sites. FIG. 6 also shows that most of the ammonia was desorbed from weak and medium acid sites and the relevant peak occurs at 208° C. (peak 1), and the corresponding volume of ammonia was found to be 9.6 cm3/g of catalyst. In contrast, the volume of ammonia that was desorbed at high temperature was found to be 2.6 cm3/g of catalyst and the relevant peak occurs at 570° C.

As previously described, catalyst acidity has a vital role in oxidative cracking, these acid sites include Bronsted and Lewis acid sites. This relatively high acidity comes from the Ce-$\gamma$-$Al_2O_3$ support surface, which contains hydroxyls as confirmed by FTIR analysis (10-15 OH per $nm^2$), the linear hydroxyls being Bronsted like ($H^+$ acceptors) and the bridged hydroxyls being $H^+$ donors [A. Haynes, Concepts of Modern Catalysis and Kinetics, vol. 2005, no. 05. 2005, pp. 851-851.—incorporated herein by reference in its entirety]. Furthermore, since alumina was activated at a high enough temperature of 400° C., but not sufficient to cause phase change, this results in dihydroxylation of Bronsted acid sites which leads to the formation of Lewis acid sites. The strong acid sites contribute to the cracking of the feed and products via C—C bond fission, which can follow carbenium or combined ion mechanisms [R. Schl, Concepts in Selective Oxidation of Small Alkane Molecules. 2009.—incorporated herein by reference in its entirety].

EXAMPLE 7

$NH_3$-Temperature Programmed Desorption ($NH_3$-TPD) Kinetics Analysis of the Prepared Catalyst The $NH_3$-TPD data was further analyzed to estimate desorption kinetic parameters (activation energy of desorption and frequency factors). These parameters are important to study catalyst surface characteristics such as metal support interactions. The property affects the nature of $VO_x$ on the surface and ultimately catalyst conversion and product selectivity. The model as described in this section was used to estimate these parameters by setting the following assumptions: (i) homogeneous catalyst surface, $k_d$=(-$E_{des}$/RT), (ii) ammonia does not re-adsorb during the experiment, (iii) uniform adsorbate concentration in the gas flow, and (iv) first order adsorption rate in surface coverage. A high gas flow rate was maintained together with appropriate conditions to satisfy the previous assumptions, and by performing species balance on desorbing $NH_3$ desorption rate can be written as formula (XI).

$$r_{des} = -V_m\left(\frac{d\theta_{des}}{dt}\right) = k_{d,o} \times \theta_{des}^n \qquad (XI)$$

FIG. 6 demonstrates that ammonia desorption follows first order rate [B. Fu, J. Lu, P. C. Stair, G. Xiao, M. C. Kung, and H. H. Kung, "Oxidative dehydrogenation of ethane over alumina-supported Pd catalysts. Effect of alumina overlayer," J. Catal., vol. 297, pp. 289-295, January 2013.—incorporated herein by reference in its entirety]. Taking this into account $E_{des}$ and $K_{des,0}$ can be obtained from formula (XII).

$$r_{des} = -V_m\left(\frac{d\theta_{des}}{dt}\right) = k_{d,0}\theta_{des}\exp\left[-\frac{E_{des}}{R}\left(\frac{1}{T}-\frac{1}{T_m}\right)\right] \qquad (XII)$$

In this formula, (i) $\theta_{des}$ is the surface coverage of the adsorbed species, (ii) $K_d$, $k_{d,0}$ are the desorption constant and pre-exponential factor respectively, (iii) $T_m$ is the centering temperature in ° C., and by rising the temperature gradually with a constant value $\beta$(one can apply formula (XIII), formula (XIV), formula (XV), formula (XVI) and formula (XVII) resulting in formula (XVIII).

$$T = T_0 + \beta t \qquad (XIII)$$

$$\frac{dT}{dt} = \beta \qquad (XIV)$$

$$\frac{d\theta_{des}}{dt} = \frac{d\theta_{des}dT}{dT\,dt} = \beta\frac{d\theta_{des}}{dT} \qquad (XV)$$

-continued $$\frac{d\theta_{des}}{dT} = -\frac{k_{des,0}}{\beta V_m}\theta_{des}\exp\left[-\frac{E_{des}}{R}\left(\frac{1}{T}-\frac{1}{T_m}\right)\right] \quad (XVI)$$

$$\theta_{des} = 1 - \frac{V_{des}}{V_m} \quad (XVII)$$

$$\frac{dV_{des}}{dT} = \frac{k_{des,0}}{\alpha}\left(1-\frac{V_{des}}{V_m}\right)\exp\left[-\frac{E_{des}}{R}\left(\frac{1}{T}-\frac{1}{T_m}\right)\right] \quad (XVIII)$$

Figure 7:
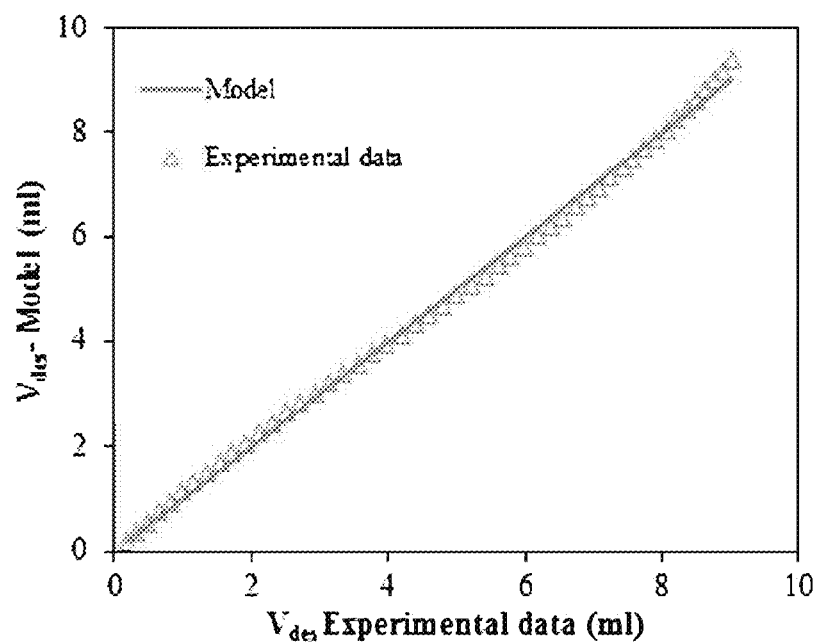
FIG. 7 is a comparison of the experimental data and fitted model of ammonia desorption during $NH_3$-TPD kinetics analysis for the prepared $VO_x$/Ce-γ-$Al_2O_3$ catalyst sample.

Formula (XVIII) was fitted to experimental data using MATLAB least square methods at a heating rate (β) taken as 10° C./min. In all experiments ammonia was pre-adsorbed at 120° C. Table 2 reports statistical validations such as confidence interval, degree of freedom, and $R^2$ value. FIG. 7 shows the model prediction using formula (XVIII) and the $NH_3$-TPD experimental data. It is evident that there is good agreement between the predicted and experimental data, which further confirms the validity of the proposed model. The activation energy for ammonia desorption from the $VO_x/Ce$-γ-$Al_2O_3$ catalyst sample was found to be 6.5 kJ, which is lower than that which has been reported for comparative exemplary catalysts. Higher activation energy indicates that the V-support interaction is stronger than the V—V interaction and therefore $VO_x$ species isolation has been reduced by formation of crystalline $VO_x$ as shown in the Raman analysis and FTIR analysis.

TABLE 2

Estimated ammonia-TPD kinetic parameters of the prepared catalyst sample

| Parameter | Value |
| --- | --- |
| $E_{des}$ | 6.5 (kJ) |
| $k_{des}$ | 0.161 (cm3/min) |
| $R^2$ | 0.998 |
| Degree of freedom | 48 |
| Confidence interval | 95% |

EXAMPLE 8

Evaluation of the Prepared Catalyst in the Fluidized Oxidative Cracking of Hexane The reactivity and stability of the $VO_x/Ce$-γ-$Al_2O_3$ catalyst sample was evaluated using a fluidized CREC (CREC: Chemical Reactor Engineering Centre) riser simulator, a laboratory scale reactor, capable of simulating various sections of a riser/downer reactor. The CREC riser simulator consists of a reactor system connected to a vacuum box through a four port valve. For product analysis, the vacuum box is connected to an online gas chromatograph (GC) by a six port valve. The reactor system consists of a chamber holding the catalyst basket, heating elements, an impeller to fluidize the catalyst and a feed injection port.

In the present disclosure, the CREC riser simulator was used to test the viability of a new catalyst for use in the fluidized bed oxidative cracking of hexane given the following: i) close control of catalyst and gas-solid reaction times, providing reaction times similar to those expected in industrial circulating fluidized bed units, ii) short contact times with the range of a few seconds, iii) careful control of the catalyst/reactant weight ratios and fluidization conditions, and iv) accurate control of reaction conditions including temperature and reactant partial pressures. The oxidative cracking (OC) of hexane experiments were conducted with the temperature varied from 525 to 600° C. while the contact timer were adjusted between 5 and 25 seconds. After each reaction run, the catalyst was regenerated by supplied air at 550° C. for 15 minutes. Therefore, the alternative reaction and catalyst regeneration were achieved without circulating the catalyst.

In a typical run, 0.85 g of oxidized $VO_x/Ce$-γ-$Al_2O_3$ catalyst sample was loaded into the reactor basket and a leak test was conducted. Following the leak test, the system was purged by flowing argon. The temperature program was started to heat the reactor to the desired temperature. The argon flow was maintained to keep the reactor from any interference caused by gas phase oxygen. Once the reactor temperature reached the desired temperature, the argon flow was discontinued. The reactor isolation valve was closed when it reached the desired pressure level. At this stage the vacuum pump was turned on to evacuate the vacuum box down to 20.7 kPa (3.75 psi). The catalyst was fluidized by rotating the impeller. At this point, the hexane feed (0.4 mL) was injected into the reactor by using a preloaded gas tight syringe. The reaction continued for a pre-specified time. At the termination point, the isolation valve between the reactor and vacuum box opened automatically and transferred all the reactants and products into the vacuum box. The gas samples in the vacuum box were analyzed using and Agilent 7890A gas chromatograph (GC) equipped with both a thermal conductivity detector (TCD) and a flame ionization detector (FID). For each catalytic run, the product samples were analyzed three times to ensure the accuracy of the analysis. Finally, the product analysis data was used to calculate the conversion and selectivity of various products. The definitions used in calculating the conversion and selectivity are represented in formula (V) and formula (VI) respectively.

$$\text{Conversion of hexane} = \frac{\text{Moles of hexane converted}}{\text{Moles of hexane fed}} \times 100\% \quad (V)$$

$$\text{Selectivity to product } i = \frac{\text{Moles of product } i}{\text{Moles of hexane converted}} \times 100\% \quad (VI)$$

Figure 8:
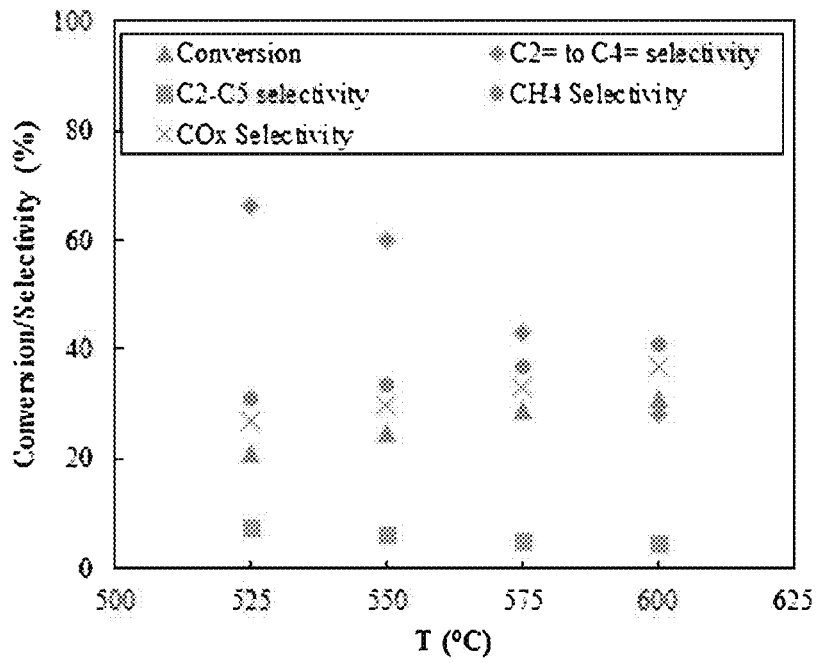
FIG. 8 is a graph of hexane ($C_6H_{14}$) conversion and $CO_x$, $CH_4$, parrafins ($C_2$ to $C_5$) and olefins ($C_2H_4$, $C_3H_6$, and $C_4H_8$) product selectivity for the prepared $VO_x$/Ce-γ-$Al_2O_3$ catalyst sample in the oxidative cracking of hexane reaction runs at a temperature range of 525-600° C., a reaction time of 15 seconds, and a hexane feed of 0.4 mL at STP illustrating the effect of temperature on the hexane conversion and product selectivity.

FIG. 8 reports the products from the oxidative cracking of n-hexane over a temperature range from 525 to 600° C. It can be seen that an increasing reaction temperature increases n-hexane conversion due to the formation of various products by cracking and dehydrogenation. Conversion of up to 31% has been obtained at 600° C., and the products from this reaction consist of short olefins ($C_2H_4$ ethylene, $C_3H_6$ propylene, and $C_4H_8$ butylene) and paraffins ($C_1$-$C_5$) together with $CO_x$ gases. In addition, the selectivity to olefins decreases with increasing temperature (66% to 28%), this can be attributed to the formation of $CH_4$ and $CO_x$ by cracking due to acidity and combustion at a high oxygen releasing rate from the catalyst surface at high temperatures. The obtained results are in agreement with the TPR and TPD analyses, which show that the $VO_x/Ce$-γ-$Al_2O_3$ catalyst has good activity in terms of $H_2$ consumption which indicates catalyst activity in ODH type reactions. With regards to cracking of hexane, the $VO_x/Ce$-γ-$Al_2O_3$ catalyst demonstrates high acidity (FIG. 6) which contributes to increasing catalyst conversion. However, high $CH_4$ and $CO_x$ amounts have been obtained due to side reactions (combustion) and harsh cracking of the feed and products.

Figure 9:
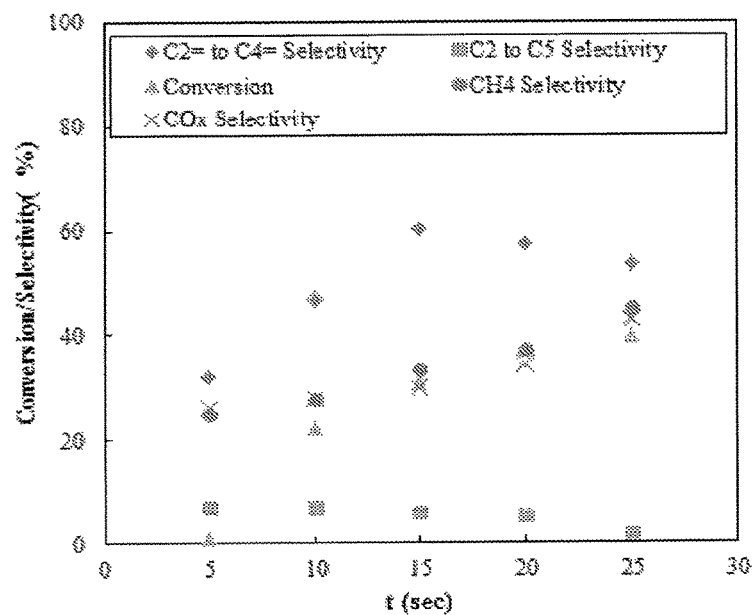
FIG. 9 is a graph of hexane ($C_6H_{14}$) conversion and $CO_x$, $CH_4$, parrafins ($C_2$ to $C_5$) and olefins ($C_2H_4$, $C_3H_6$, and $C_4H_8$) product selectivity for the prepared $VO_x$/Ce-γ-$Al_2O_3$ catalyst sample in the oxidative cracking of hexane reaction runs at a reaction time range of 5-25 seconds, a reaction temperature of 550° C., and a hexane feed of 0.4 mL at STP illustrating the effect of reaction time on the hexane conversion and product selectivity.

FIG. 9 shows products selectivity and conversion from the oxidative cracking of n-hexane over time at a reaction temperature of 550° C. It can be seen that olefins selectivity reaches up to 60% at 15 seconds, which is notably higher than other products (i.e. alkanes, $CH_4$ and $CO_x$). This data confirms the excellent selectivity to olefins of the $VO_x$/Ce-γ-$Al_2O_3$ catalyst, which can be attributed to several factors, such as (i) role of the catalyst in dehydrogenation of cracking products and (ii) controlled release of $O_2$ from the catalyst surface. In addition, it has been reported that the oxygen amount inside the reactor affects product selectivity severely by increasing combustion products. In oxidative cracking, olefins are produced by cracking and dehydrogenation; thus, the type of $O_2$ species present also have a large role in the conversion of saturated hydrocarbons into olefins. In this regard, the catalyst surface usually contains different types of oxygen species (electrophilic and nucleophilic), these $O_2$ species can be formed depending on metal support interactions and the type of bonds formed. Furthermore, vanadium has the ability to form different types of bonds on an alumina surface such as V—O—V, V=O, and V—O—Al as confirmed by the Raman and FTIR results. The V—O—Al bond has been reported to have the most active and selective oxygen for dehydrogenation, this may offer an explanation for the observed catalyst selectivity to olefins (FIG. 9). FIG. 9 also shows that the $VO_x$/Ce-γ-$Al_2O_3$ catalyst demonstrates good stability during the oxidative cracking reaction in agreement with the TPR/TPO cycles which showed catalyst thermal stability and confirmed the stability of $VO_x$ species on the support.

The products from oxidative cracking in a gas phase oxygen free environment are different from those that have been obtained via gas phase oxygen cracking. Previously published literature reports have shown low selectivity to light olefins (ethylene and propylene) when gas phase oxygen is introduced directly into the reactor. Table 3 shows a typical products distribution in an oxidative cracking reaction run in a gas phase oxygen free environment. It can be noted that good selectivity to olefins ($C_2^=$ to $C_4^=$) has been obtained (60%) as previously described. In addition, selectivity to ethylene and propylene is higher than other products such as butylene and paraffins. This can be attributed to catalyst contribution to the dehydrogenation reaction, through which paraffins are converted into olefins as shown in FIG. 1. However, considerable amounts of $CO_x$ and $CH_4$ are obtained due to combustion and harsh cracking as previously described at high temperatures.

TABLE 3

Oxidative cracking of hexane reaction products distribution (reaction time = 15 seconds, hexane feed = 0.4 mL at STP)

| | Reaction temperature (° C.) | | | |
|---|---|---|---|---|
| | 525 | 550 | 575 | 600 |
| Hexane conversion (mole %) | 21 | 25 | 29 | 31 |
| Product selectivity (mole %) | | | | |
| $CH_4$ | 31 | 33.5 | 37 | 41 |
| $C_2H_4$ | 14.3 | 15.2 | 11.4 | 9.4 |
| $C_3H_6$ | 10.4 | 6.14 | 3.76 | 2.0 |
| $C_4H_8$ | 8.5 | 5.7 | 4.4 | 3.29 |
| $C_2H_6$ | 1.25 | 2.0 | 2.68 | 3.9 |
| $C_3H_8$ | 3.9 | 1.5 | 2.08 | 2.6 |
| $C_4H_{10}$ | 1.59 | 1.2 | 0.95 | 0.82 |
| $C_5H_{12}$ | 0.63 | 0.42 | 0.28 | 0.17 |
| $CO_x$ | 27 | 30 | 33 | 37 |

Figure 10:
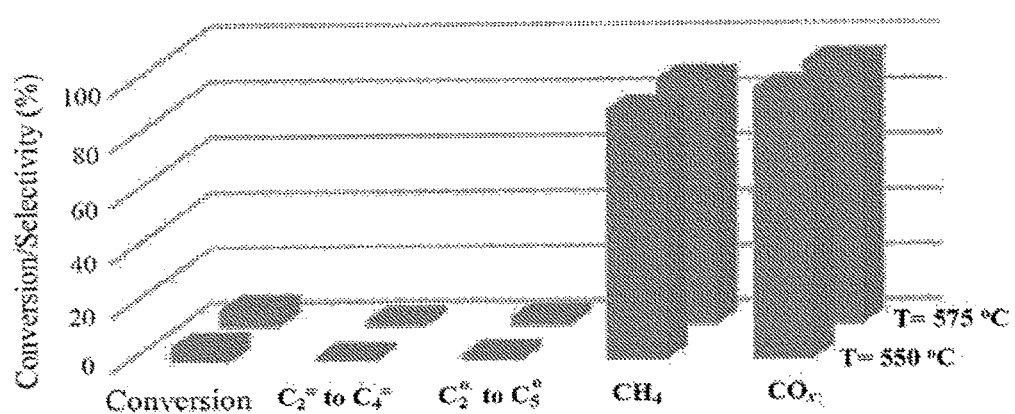
FIG. 10 is graph of hexane ($C_6H_{14}$) conversion and $CO_x$, $CH_4$, parrafins ($C_2$ to $C_5$) and olefins ($C_2H_4$, $C_3H_6$, and $C_4H_8$) product selectivity for the prepared $VO_x$/Ce-γ-$Al_2O_3$ catalyst sample without regeneration in the oxidative cracking of hexane reaction runs at reaction temperatures of 550° C. and 575° C., a reaction time of 15 seconds, and a hexane feed of 0.4 mL at STP illustrating the effect of lacking surface oxygen on the hexane conversion and products selectivity.

Oxidative cracking experiments were further conducted using the reduced form of the catalyst and in the absence of air in order to assess the role of thermal cracking. Pure hexane was injected into the reactor at reaction temperatures of 550 and 575° C. for a reaction time of 15 seconds. FIG. 10 shows the reaction products without catalyst regeneration. Thus, the only products that were obtained are $CO_x$ gases which were produced from combustion and a fraction of $CH_4$ due to thermal cracking. In addition, the conversion of hexane is almost negligible in the absence of the catalyst. The absence of surface oxygen which is available from $VO_x$ on catalyst support severely affects the reaction products formed. This was previously confirmed by the TPR/TPO cycles which show that the presence or reducible vanadium is essential for $H_2$ consumption. Furthermore, previously published literature reports have presented similar conclusions regarding the $VO_x$ reduction effect. This can be attributed to the nature of $VO_x$ species formed on the surface and the types of bonds present.

The oxide phase is responsible for the overall catalytic activity and selectivity such as $VO_x$ species, compared to $Nb_2O_5$ and β-$(Nb,V)_2O_5$ [E. Heracleous and a Lemonidou, "Ni—Nb—O mixed oxides as highly active and selective catalysts for ethene production via ethane oxidative dehydrogenation. Part II: Mechanistic aspects and kinetic modeling," *J. Catal.*, vol. 237, no. 1, pp. 175-189, January 2006.—incorporated herein by reference in its entirety]. However, the crystalline $V_2O_5$ phase only has a small contribution to the catalyst and a minor effect on the catalytic activity and selectivity. The multiple peaks in the TPR analysis also indicate the presence of several types of oxides in agreement with the XRD and Raman analysis results. With regards to the mechanisms of phase transformation of vanadia species, it is reported that these species usually form during the reduction steps, which create oxygen vacancies at the surface. When the concentration of the oxygen vacancies surpasses a certain critical value, the vacancies aggregate into a vacancy disc, called a shear plane. Part of vanadium oxide may shear so that along the shear plane the linkage between trigonal bipyramids is changed from corner-sharing into edge-sharing. Thus, another stable structure is formed, which is stoichiometrically different from the original structure.

It is of value to compare different types of catalysts for the oxidative catalytic cracking of n-hexane to investigate the effect of different reaction conditions, catalyst compositions and reaction mechanisms. Table 4 presents differetypes of catalysts which have been used for the oxidative catalytic cracking of n-hexane including zeolites and metal oxides. Although different reaction setups may have been used, the presence of gas phase oxygen and the effect of the dehydrogenation reaction are of primary interest. For example, Del-Al-MCM-22 zeolite gives up to 95% conversion, this is largely due to high acidity and a surface area value of 448 $m^2/g$, which is proportional to catalyst activity. However, no dehydrogenation reaction takes place, thus the cracking reaction is the major source of olefins, and consequently only a 40% olefins selectivity has been achieved. In contrast, the dehydrogenation reaction is reported to accompany the cracking reaction when metal oxides such as $MoO_2$ are used for the hexane cracking. A low conversion of 2% was obtained, although a higher selectivity to olefins was achieved (Table 4). This can be attributed to the low acidity of the catalyst and insufficient acid sites available for cracking. Alternatively, supported metal oxides have been implemented for oxidative cracking, such as $Pt/MgAl_2O_4$, with the intention that alumina has high acidity and surface area compared to metal oxides. High catalyst activity has been achieved (90% conversion) using $Pt/MgAl_2O_4$ and high olefins selectivity as well (70%); although, this high selectivity was obtained only by introducing $H_2$ and also at a high temperature of 850° C. Similarly, gas phase oxidative cracking has been studied versus catalytic oxidative cracking over Li/MgO. Boyadjian, et al. have reported that increasing gas phase oxygen decreases selectivity to olefins.

TABLE 4

Comparison of the performance of the prepared $VO_x$/CaO-γ-$Al_2O_3$ (1:1) catalyst with that of other ODH catalysts previously reported in the literature

| Catalyst | Conversion | Olefin selectivity | Feed | Reference |
|---|---|---|---|---|
| Del-Al-MCM-22 | 40% | 90% | W/F n-hexane = 6.4-64 g-cat h/mol-n-hexane, t = 15 min | Yong Wang, 2015 |
| $MoO_2$ | 2% | Ethylene 29% Propylene 35% Butylene 19% | n-hexane, pressure 7.3 Torr | Jae Hee Song, 2002 |
| 0.1% Pt/$MgAl_2O_4$ | 90% | 70% light olefins | $C_6/O_2/N_2$ = Dec. 15, 1993 (mL/min, STP), GHSV = 30,000 h 1 | X. Liu, et al., 2004 |
| Li/MgO | 28% | 60% light olefins | 100 mL/min, 10% hexane, 8% oxygen and balance He; WHSV = 15.4 h1 | Cassia |
| $VO_x$/Ce-γ-$Al_2O_3$ | 25% | 60% light olefins | 0.4 mL hexane, 0.85 g catalyst | Current Disclosure |

In general, dehydrogenation improves olefins selectivity in oxidative cracking: however, it can be seen that strong acidity and high surface area are also major factors that affect the conversion. Additionally, in contrast with previously studied catalysts, no hydrogen supply was need for the reaction with the $VO_x$/Ce-γ-$Al_2O_3$ catalyst sample. Furthermore, the type of oxygen involved in the oxidative cracking has a large effect on olefins selectivity. In the context of gas phase oxygen free oxidative cracking the source of $O_2$ is the lattice oxygen of the catalyst. The lattice oxygen content is present is the form of nucleophilic ($O^{2-}$, $O^-$) and electrophilic ($O_2^-$) forms and they are selective to different oxidation products. In early stages, the release of oxygen favors olefins formation. With increasing reaction time, the oxygen released by the catalyst allows the formation of more $CO_x$ products. Therefore, activation of C—H bonds of alkane mainly depends on the catalyst and oxygen active species present on the surface which eventually affect the olefin selectivity.

In conclusion, the $VO_x$/Ce-γ-$Al_2O_3$ catalyst sample for oxidative cracking of hexane to light olefins (i.e. ethylene, propylene, butylene) was investigated. The synthesized catalyst samples were characterized using a variety of physiochemical techniques. The gas phase oxygen free oxidative cracking reactions were performed in a CREC riser simulator under various reaction conditions. XRD patterns show peaks of amorphous and crystalline $VO_x$, which were confirmed by FTIR and Raman analysis as both V—O—V and V—O—Al bonds were detected representing crystalline and isolated $VO_x$ respectively. TPR/TPO oxidation-reduction cycles demonstrate good catalyst stability and the $VO_x$ species were found to be active $H_2$ consumption with 78% reducible vanadium content. $NH_3$-TPD analysis shows high acidity which was found to be 12.2 $cm^3$ $NH_3$/g of catalyst and desorption kinetics established using a first order desorption model calculate a desorption energy of 6.5 kJ, the low desorption energy indicating the presence of the V—V interaction. Reactivity tests in the CREC riser simulator show good hexane conversion of 25% and 66% olefins selectivity at 550° C. reaction temperature and a reaction time of 15 seconds. In addition, no gas phase oxygen or H2 gases were used in the $VO_x$/Ce-γ-$Al_2O_3$ catalyst reaction. Oxidative dehydrogenation improved catalyst activity by activation of hexane and increased olefins selectivity as a result of controlled catalyst lattice oxygen contribution.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for the oxidative cracking of an alkane to produce one or more olefins comprising:
    flowing the alkane through a fluidized bed reactor comprising a catalyst chamber loaded with a catalyst at a temperature in the range of 450-700° C. to form the one or more olefins and a reduced catalyst, wherein the alkane is a $C_2$-$C_8$, straight chain linear alkane,
    wherein the catalyst comprises:
    a support material comprising alumina modified by cerium; and
    a catalytic material comprising one or more vanadium oxides disposed on the support material;
    wherein the catalyst comprises 1-15% of the one or more selected from the group consisting of $V_2O_5$, $VO_2$, and $V_2O_3$ by weight relative to the total weight of the catalyst, and
    wherein the catalyst comprises 0.05-1.0% of cerium by weight relative to the total weight of the catalyst.

2. The method of claim 1, wherein the alkane is hexane and the one or more olefins comprise at least one of ethylene, propylene, butylene and mixtures thereof.

3. The method of claim 1, further comprising:
    oxidizing at least a portion of the reduced catalyst by flowing air through the catalyst chamber to regenerate the catalyst; and
    repeating the flowing and the oxidizing at least once with a less than 15% decrease in percent conversion of the alkane, a less than 15% decrease in selectivity for the one or more olefins relative to a total percentage of products formed, or both.

4. The method of claim 1, wherein the catalyst is present at an amount in the range of 0.50-2.5 g of catalyst per mL, of alkane.

5. The method of claim 1, wherein the alkane is hexane and the method has a hexane conversion of 5-50 mol % at a reaction time of 1-40 seconds and a temperature of 500-650° C.

6. The method of claim 1, wherein the alkane is hexane and the method has a short olefins selectivity defined as moles of ethylene, propylene, and butylene produced per moles of hexane converted of 20-70% at a reaction time of 1-40 seconds and a temperature of 500-650° C.

7. The method of claim 1, wherein the alkane is hexane and the method has a $CO_x$ selectivity defined as moles of carbon monoxide and carbon dioxide produced per moles of hexane converted of no more than 50% at a reaction time of 1-40 seconds and a temperature of 500-650° C.

8. The method of claim 1, wherein the alkane is hexane and the method has a short olefins selectivity defined as moles of ethylene, propylene, and butylene produced per moles of hexane converted of at least 60% at a reaction time of 1-40 seconds and a temperature of 500-650° C.

9. The method of claim 1, wherein the one or more vanadium oxides form an amorphous phase on the surface of the support material.

10. The method of claim 1, wherein the one or more vanadium oxides form a crystalline phase on the surface of the support material.

11. The method of claim 1, wherein the catalyst comprises at least 50% of $V_2O_5$ by weight relative to the total weight of the one or more vanadium oxides.

12. The method of claim 1, wherein the catalyst has an average particle size in the range of 20-160 μm.

13. The method of claim 1, wherein the catalyst has an apparent particle density in the range of 1-10 g/cm$^3$.

14. The method of claim 1, wherein the catalyst has a BET surface area in the range of 25-400 m$^2$/g.

\* \* \* \* \*